United States Patent
Broering et al.

(10) Patent No.: US 10,421,812 B2
(45) Date of Patent: Sep. 24, 2019

(54) ISOFORM SPECIFIC SOLUBLE FMS-LIKE TYROSINE KINASE (SFLT) BINDING AGENTS AND USES THEREOF

(71) Applicant: University of Massachusetts, Boston, MA (US)

(72) Inventors: Teresa Broering, Brookline, MA (US); Colby Souders, North Weymouth, MA (US); Gregory Babcock, Marlborough, MA (US); Naomi Boatright, Quincy, MA (US)

(73) Assignee: University of Massachusetts, Boston, MA (US)

( * ) Notice: Subject to any disclaimer, the term of this patent is extended or adjusted under 35 U.S.C. 154(b) by 633 days.

(21) Appl. No.: 15/086,445

(22) Filed: Mar. 31, 2016

(65) Prior Publication Data

US 2016/0347843 A1    Dec. 1, 2016

Related U.S. Application Data

(60) Provisional application No. 62/141,203, filed on Mar. 31, 2015.

(51) Int. Cl.
| | | |
|---|---|---|
| *C07K 16/28* | (2006.01) | |
| *G01N 33/68* | (2006.01) | |
| *C07K 16/40* | (2006.01) | |
| *C07H 1/00* | (2006.01) | |

(52) U.S. Cl.
CPC .......... *C07K 16/2863* (2013.01); *C07H 1/00* (2013.01); *C07K 16/40* (2013.01); *G01N 33/689* (2013.01); *C07K 2317/21* (2013.01); *C07K 2317/92* (2013.01); *G01N 2333/71* (2013.01); *G01N 2800/368* (2013.01)

(58) Field of Classification Search
None
See application file for complete search history.

(56) References Cited

PUBLICATIONS

Souders et al., Circulating Levels of sFlt1 Splice Variants as Predictive Markers for the Development of Preeclampsia. Int J Mol Sci. Jun. 2, 2015;16(6):12436-53. doi: 10.3390/ijms160612436.

*Primary Examiner* — Bao Thuy L Nguyen
*Assistant Examiner* — Ellen J Marcsisin
(74) *Attorney, Agent, or Firm* — Wolf, Greenfield & Sacks, P.C.

(57) ABSTRACT

Aspects of the present disclosure relate to binding agents (e.g., antibodies and antigen binding fragments) that bind soluble fms-like tyrosine kinase 1 (sFlt1) in an isoform specific manner. In some embodiments, immunological assay methods utilizing isoform-specific antibodies or antigen binding fragments that bind sFlt1 isoforms are provided for assessing biological samples obtained from pregnant subjects, e.g., for purposes of evaluating preeclampsia status in the subject.

12 Claims, 11 Drawing Sheets
Specification includes a Sequence Listing.

FIG. 1A

14-pep1          KLH--CDQEAPYLLRNLSDH
TRX-Exon14       TRX--DQEAPYLLRNLSDHTVAISSSTTLDCHANGVPEPQITWFKNNHKIQQEP
sFlt1-C          KLH--CNKKAVFSRISKFKSTRN
GST-1C           GST--FHCNKKAVFSRISKFKSTRNDCTTQSNVKH

FIG. 1B sFlt1-14  [1][2][3][4][5][6][7]
sFlt1-14-human (651) KEITIRDQEAPYLLRNLSDHTVAISSSTTLDCHANGVPEPQITWFKNNHKIQQEPG 706
sFlt1-1-human  (651) KEITIRGEHC--N--KKAVFSRISKFKSTRNDCTTQSNVKH sFlt1-1  [1][2][3][4][5][6]

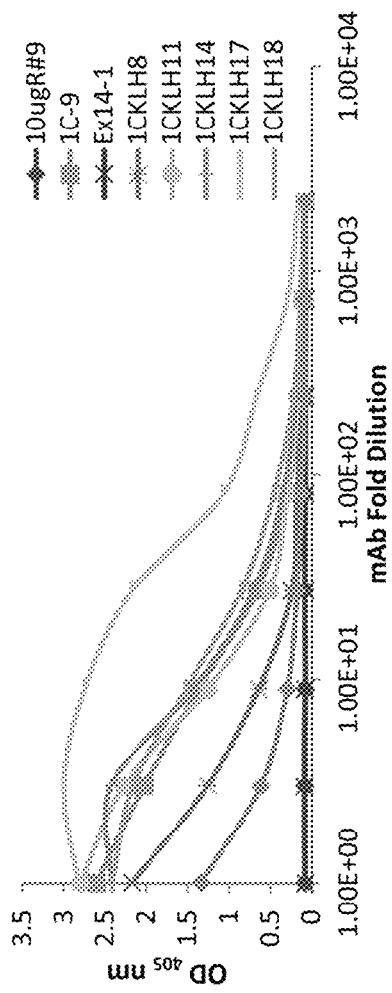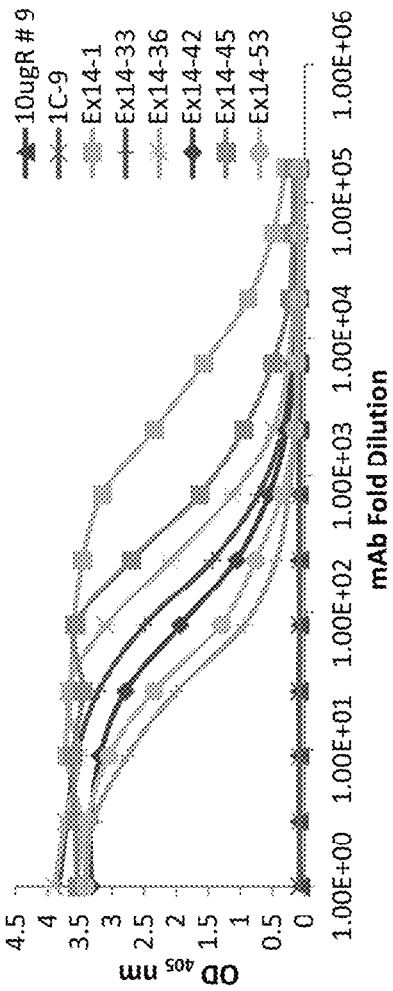
FIG. 2A
FIG. 2B

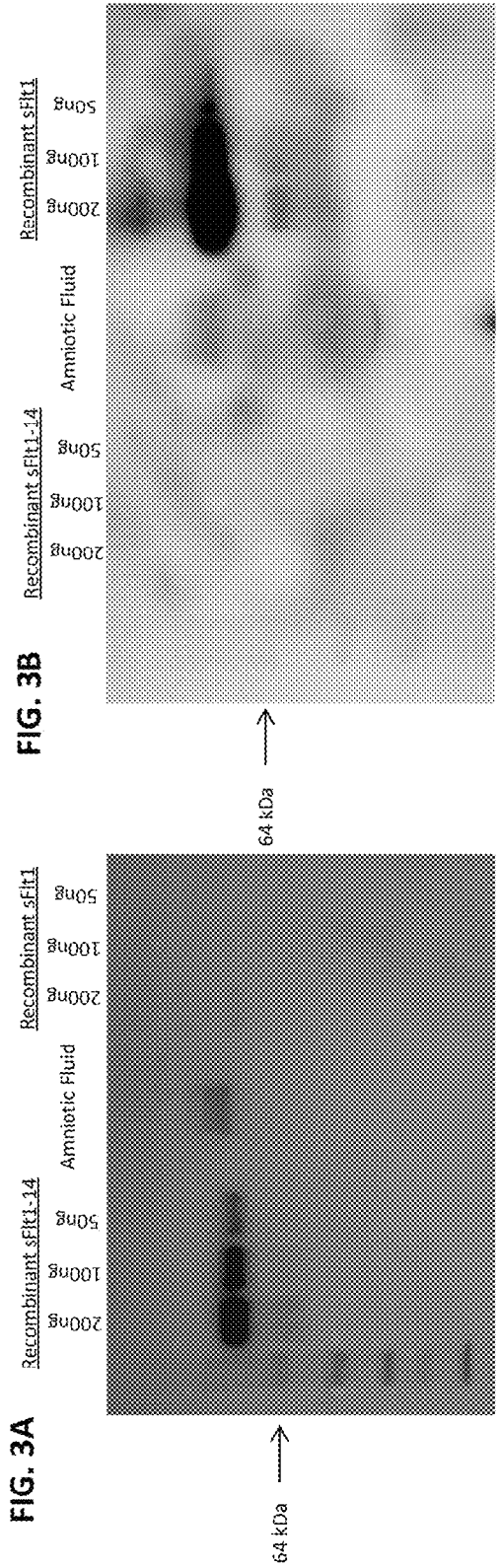
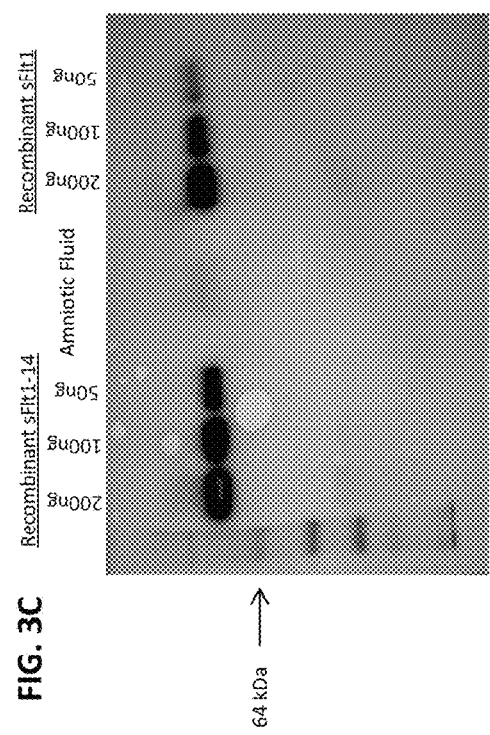
FIG. 3A
FIG. 3B
FIG. 3C

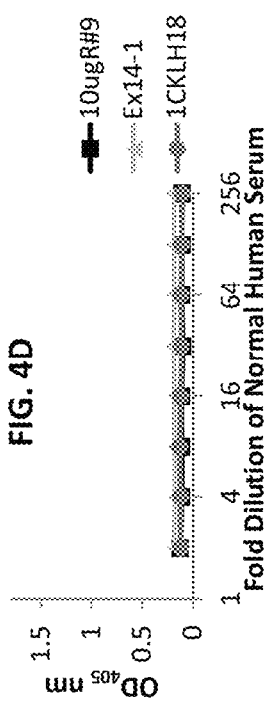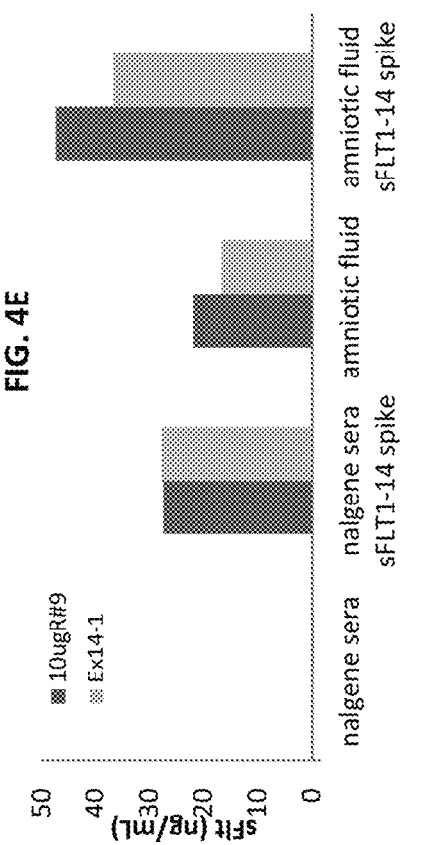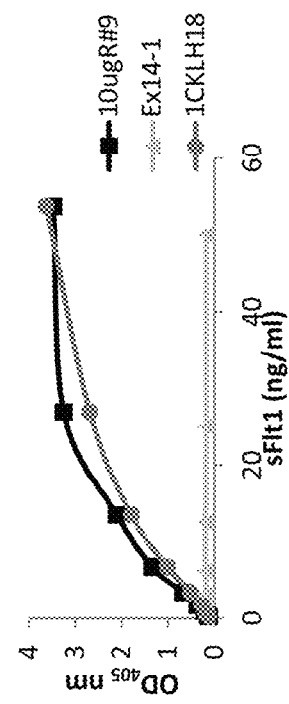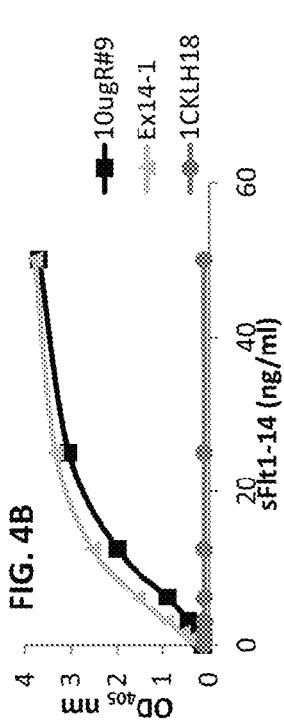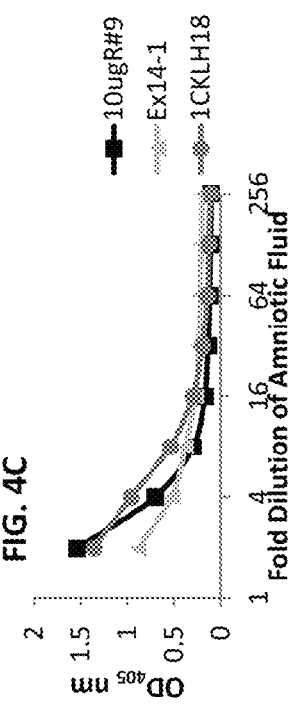
FIG. 4A
FIG. 4B
FIG. 4C
FIG. 4D
FIG. 4E

FIG. 6

Anti-human sFlt1-specific variant mouse MAb 1C-KLH-18 VH

V segment: Musmus IGHV1.4-4
D segment: Musmus IGHD2-4
J segment: Musmus IGHJ4

SEQ ID NO:1

```
      E   V   Q   L   Q   Q   S   G   A   E   L   V   R   P   G   A   S
    1 GAG GTT CAG CTG CAG CAG TCT GGG GCT GAG CTT GTG AGG CCA GGG GCC TCA
```

SEQ ID NO:2                                            CDR1 SEQ ID NO:3 (aa) 4 (nt)

```
      V   K   L   S   C   T   A   S   G   V   N   I   K   D   Y   Y   M
   52 GTC AAG TTG TCC TGC ACA GCT TCT GGC GTT AAT ATT AAA GAC TAT ATG
      CDR1
```

```
      N   W   V   N   Q   R   P   E   Q   G   L   E   W   I   G   W   I
  103 AAT TGG GTG AAT CAG AGG CCT GAA CAG GGC CTG GAG TGG ATT GGA ATT
      CDR2 SEQ ID NO:5 (aa) 6 (nt)
```

```
      D   P   E   N   G   D   T   E   Y   A   S   K   F   Q   G   K   A
  154 GAT CCT GAG AAT GGT GAT ACT GAA TAC GCC TCC AAG TTC CAG GGC AAG GCC
```

```
      T   I   T   A   D   T   S   S   N   T   A   Y   Y   C   A   Y   S
  205 ACT ATA ACA GCA GAC ACA TCC AGC AAC ACA GCC TAC TAC TGT GCT AGC
                                                                CDR3
```

```
      L   T   S   E   D   T   A   E   D   T   A   V   Y   Y   C   A   R
  256 CTG ACA TCT GAG GAC ACT GCT GTC TAT TAC TGT GCA AGA
```

CDR3 SEQ ID NO:7 (aa) 8 (nt)

```
      F   P   F   Y   W   G   Q   G   T   L   V   S   V   S   A
  307 TTC CCC TTT GTT TAC TGG GGC CAA GGG ACT CTG GTC TCT GCA
```

FIG. 7

Anti-human sFlt1-specific variant mouse MAb 1C-KLH-18 vK

V segment: Musmus IGKV1-117
J segment: Musmus IGKJ4

SEQ ID NO:9

SEQ ID NO:10

```
      D   V   L   M   S   Q   T   P   L   S   L   P   V   S   L   G   D
  1  GAT GTT TTG ATG TCC CAA ACT CCA CTC TCC CTG CCT GTC AGT CTT GGA GAT
                                   CDR1 SEQ ID NO:11 (aa)  12 (nt)
      Q   A   S   I   S   C   R   S   S   Q   N   I   V   H   S   N   G
 52  CAA GCC TCC ATC TCT TGC AGA TCT AGT CAG AAC ATT GTA CAT AGT AAT GGA
     CDR1
          ~~~~~~~~~~~~~~~~~~~~~~~~~~~~~~~~~~~~~~~~~~~~~~~~~~~~~~~~~~~~
      N   T   Y   L   E   W   Y   L   Q   K   P   G   Q   S   P   K   L
103  AAC ACC TAT TTA GAA TGG TAC CTG CAG AAA CCA GGC CAG TCT CCA AAG CTC
              ~~~~~~~~~~~~~~~~~~~~~~~
                        CDR2 SEQ ID NO:13 (aa)  14 (nt)
      L   I   H   K   V   S   N   R   F   S   G   V   P   D   R   F   S
154  CTG ATC CAC AAA GTT TCC AAC CGA TTT TCT GGG GTC CCA GAC AGG TTC AGT
         ~~~~~~~~~~~~~~~~~~~~~
      G   S   G   S   G   T   D   F   T   L   K   I   S   R   V   E   A
205  GGC AGT GGA TCA GGG ACA GAT TTC ACA CTC AAG ATC AGC AGA GTG GAG GCT
                                   CDR3 SEQ ID NO:15 (aa)  16 (nt)
      E   D   L   G   V   Y   Y   C   F   Q   G   S   H   V   P   F   T
256  GAG GAT CTG GGA GTT TAT TAC TGC TTT CAA GGT TCA CAT GTT CCA TTC ACG
                                   ~~~~~~~~~~~~~~~~~~~~~~~~~~~~~~~~~~~~
      F   G   S   G   T   K   L   E   K   K
307  TTC GGC TCG GGG ACT AAG TTG GAA AAA AAA
     ~~~~~~~~~~~
```

FIG. 8

Anti-human sFlt1-14-specific variant (binds exon 14) mouse MAb Ex14-1 VH

V segment: Musmus IGHV9-3
D segment: Musmus IGHD5-2
J segment: Musmus IGHJ3

SEQ ID NO:17

SEQ ID NO:18

```
     H   I   Q   L   V   Q   S   G   P   E   L   K   K   P   G   E   T
  1  CAT ATC CAG TTG GTA CAG TCT GGA CCT GAG TTG AAG AAG CCT GGA GAG ACA
                                     CDR1 SEQ ID NO:19  20 (aa)   (nt)
     V   K   I   S   C   K   Q   S   G   Y   I   F   T   T   S   G   M
 52  GTC AAG ATC TCC TGC AAG CAG TCT GGG TAT ATT TTC ACA ACC TCT GGA ATG
     CDR1                                                         CDR2
     S   W   V   K   Q   A   P   G   K   G   L   Q   W   M   G   W   I
103  AGC TGG GTG AAA CAG GCT CCA GGA AAG GGT TTA CAG TGG ATG GGC TGG ATA
                    CDR2 SEQ ID NO:21  22 (aa)   (nt)

N   T   Y   S   G   E   P   T   Y   A   D   D   F   K   G   R   F
154  AAC ACC TAT TCT GGA GAG CCG ACA TAT GCT GAT GAC TTC AAG GGA CGG TTT

A   F   S   L   E   T   S   A   S   T   A   Y   L   H   I   N   D
205  GCC TTC TCT TTG GAA ACC TCT GCC AGC ACT GCC TAT TTG CAC ATC AAC GAC
                                                                 CDR3
     L   K   N   E   D   T   A   T   Y   F   C   A   R   S   R   N   N
256  CTC AAA AAT GAG GAC ACG GCC ACA TAT TTC TGT GCA AGA TCT AGG AAT AAC
     CDR3 SEQ ID NO:23  24 (aa)   (nt)
     Y   E   G   F   Y   A   Y   W   G   Q   G   T   L   V   T   V   S
307  TAC GAG GGG TTT TAC GCT TAC TGG GGC CAA GGG ACT CTG GTC ACT GTC TCT
```

FIG. 9

Anti-human sFlt1-14-specific variant (binds exon 14) mouse MAb Ex14-1 VK

V segment: Musmus IGKV8-30
J segment: Musmus IGKJ5

SEQ ID NO:25

```
        D   I   V   M   S   Q   F   P   S   S   L   A   V   S   V   G   E
SEQ ID NO:26
    1 GAC ATT GTG ATG TCA CAG TTT CCA TCC TCC CTA GCT GTG TCA GTT GGA GAG
                                      CDR1 SEQ ID NO:27 (aa) 28 (nt)
        K   V   T   M   T   C   K   S   S   Q   S   L   L   Y   S   S   N
   52 AAG GTT ACT ATG ACT TGC AAG TCC AGT CAG AGC CTT TTA TAT AGT AGT AAT
                 CDR1
        Q   K   N   Y   L   A   W   F   Q   Q   K   P   G   Q   S   P   K
  103 CAA AAG AAT TAT TTG GCC TGG TTC CAG CAG AAA CCC GGG CAG TCT CCT AAA
                                CDR2 SEQ ID NO:29 (aa) 30 (nt)
        L   L   I   Y   W   A   S   T   R   E   S   G   V   P   D   R   F
  154 CTA CTG ATT TAC TGG GCA TCC ACT AGG GAA TCT GGG GTC CCT GAT CGC TTC
        T   G   S   G   S   G   T   D   F   T   L   T   I   S   S   V   K
  205 ACA GGC AGT GGA TCT GGG ACA GAT TTC ACT CTC ACC ATC AGC AGT GTG AAG
        A   E   D   L   A   V   Y   Y   C   Q   Q   Y   Y   L   Y   P   L
  256 GCT GAA GAC CTG GCA GTT TAT TAC TGT CAG CAA TAT TAT CTC TAT CCG CTC
                                                   CDR3 SEQ ID NO:31 (aa) 32 (nt)
        T   F   G   A   G   T   K   L   E   L   K
  307 ACG TTC GGT GCT GGG ACC AAG CTG GAG CTG AAA
                            CDR3
```

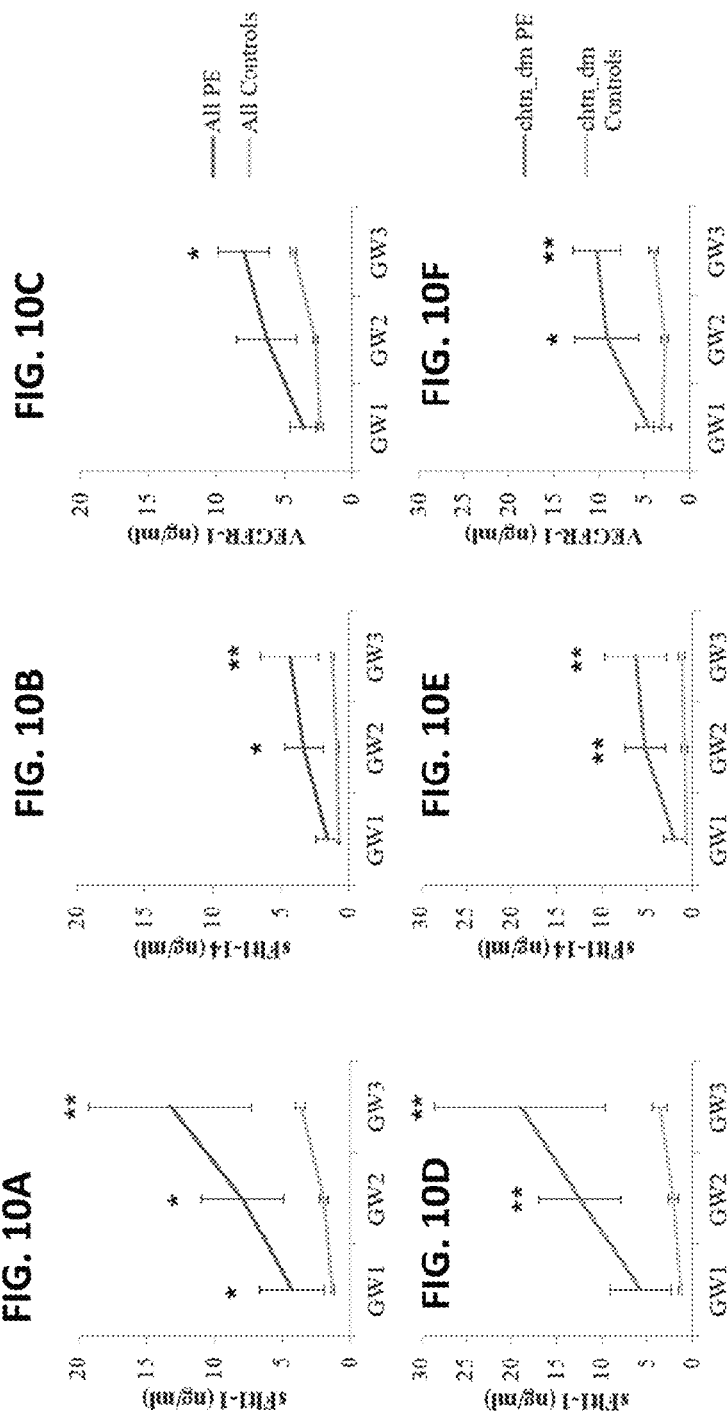

ISOFORM SPECIFIC SOLUBLE FMS-LIKE TYROSINE KINASE (SFLT) BINDING AGENTS AND USES THEREOF

RELATED APPLICATIONS

This application claims the benefit under 35 U.S.C. § 119(e) of U.S. provisional application U.S. Ser. No. 62/141,203, filed on Mar. 31, 2015, entitled "ISOFORM SPECIFIC SOLUBLE FMS-LIKE TYROSINE KINASE (sFlt) BINDING AGENTS AND USES THEREOF", the entire content of which is incorporated by reference herein.

FEDERALLY SPONSORED RESEARCH

This invention was made with government support under Grant No. UL1TR000161 awarded by the National Center for Advancing Translational Sciences of the National Institutes of Health. The government has certain rights in the invention.

BACKGROUND OF THE DISCLOSURE

Preeclampsia is a multi-system disorder characterized by hypertension, edema and proteinuria impacting between 5 and 10% of pregnancies, typically after week 20. A subset of cases progress to severe preeclampsia, with symptoms comprising severe hypertension, severe proteinuria and/or evidence of dysfunctions of the nervous system, liver, kidneys as well as fetal growth restriction. Women with severe preeclampsia have elevated risk of life-threatening events, including placental abruption, acute renal failure, cerebral hemorrhage, hepatic failure or rupture, pulmonary edema, disseminated intravascular coagulation, and progression to grand mal seizures (eclampsia).

In the United States, preeclampsia/eclampsia is one of the leading causes of maternal death, while globally more than one in ten deaths related to obstetric complications is attributable to preeclampsia/eclampsia. As well as the extension of acute risk to the mother into the post-partum period until the complete delivery of the placenta, a number of long-term pathologies have been associated with preeclampsia.

While the presence, absence and severity of preeclampsia in previous pregnancies, family history, maternal age and a number of other conditions have been identified as risk factors, preeclampsia occurs in many nulliparous pregnancies without obvious predisposing factors. In addition, the diagnosis can be complicated by superimposition of preexisting hypertension as well as the drop in blood pressure often associated with early pregnancy. Both of these factors can confound the accurate establishment of a baseline blood pressure in some patients. Similarly, preexisting renal disease, which may or may not be exacerbated by pregnancy, can confound the establishment of an appropriate baseline measure for proteinuria. Some other conditions, including but not limited to gestational hypertension, can present as one or more of the signs and symptoms associated with preeclampsia, and collectively these together with preexisting renal disease and hypertension when confused with, or superimposed upon preeclampsia, pose challenges to the proper management of the pregnant patient.

SUMMARY OF THE DISCLOSURE

Aspects of the present disclosure relate to binding agents (e.g., antibodies and antigen binding fragments) that bind soluble fms-like tyrosine kinase 1 (sFlt1) in an isoform specific manner. In some embodiments, binding agents are provided for detecting at least two isoforms, sFlt1-1 (also known as sFlt1_v1 and sFlt1-i13) and sFlt1-14 (also known as sFlt1_v2 or sFlt1-e15a), which are expressed and distributed in human tissues, particularly in pregnant women. In some embodiments, sFlt1 isoforms are stronger predictive biomarkers of preeclampsia as compared to total sFlt1 measurement, particularly in women with known risk factors for this disorder. Thus, in some embodiments, binding agents provided herein are useful for evaluating and predicting preeclampsia status in pregnant women with high sensitivity. Furthermore, certain aspects of the disclosure relate to development of sFlt1 isoform-specific monoclonal antibodies useful for assessing the relative abundance of sFlt1 isoforms within pre-defined gestational windows.

Aspects of the disclosure relate to a monoclonal antibody, or antigen binding fragment, that specifically binds to sFlt1 protein and that comprises six complementarity determining regions (CDRs): CDRH1, CDRH2, CDRH3, CDRL1, CDRL2, and CDRL3.

In some embodiments, CDRH1 comprises a sequence as set forth in SEQ ID NO: 3. In some embodiments, CDRH2 comprises a sequence as set forth in SEQ ID NO: 5. In some embodiments, CDRH3 comprises a sequence as set forth in SEQ ID NO: 7. CDRL1 comprises a sequence as set forth in SEQ ID NO: 11. In some embodiments, CDRL2 comprises a sequence as set forth in SEQ ID NO: 13. In some embodiments, CDRL3 comprises a sequence as set forth in SEQ ID NO: 15. For example, in some embodiments, CDRH1 comprises a sequence as set forth in SEQ ID NO: 3, CDRH2 comprises a sequence as set forth in SEQ ID NO: 5, CDRH3 comprises a sequence as set forth in SEQ ID NO: 7, CDRL1 comprises a sequence as set forth in SEQ ID NO: 11, CDRL2 comprises a sequence as set forth in SEQ ID NO: 13, and CDRL3 comprises a sequence as set forth in SEQ ID NO: 15, and the monoclonal antibody binds specifically to sFlt1 variant 1 (sFlt1-1).

In some embodiments, CDRH1 comprises a sequence as set forth in SEQ ID NO: 19. In some embodiments, CDRH2 comprises a sequence as set forth in SEQ ID NO: 21. In some embodiments, CDRH3 comprises a sequence as set forth in SEQ ID NO: 23. In some embodiments, CDRL1 comprises a sequence as set forth in SEQ ID NO: 27. In some embodiments, CDRL2 comprises a sequence as set forth in SEQ ID NO: 29. In some embodiments, CDRL3 comprises a sequence as set forth in SEQ ID NO: 31. For example, in some embodiments, CDRH1 comprises a sequence as set forth in SEQ ID NO: 19, CDRH2 comprises a sequence as set forth in SEQ ID NO: 21, CDRH3 comprises a sequence as set forth in SEQ ID NO: 23, CDRL1 comprises a sequence as set forth in SEQ ID NO: 27, CDRL2 comprises a sequence as set forth in SEQ ID NO: 29, and CDRL3 comprises a sequence as set forth in SEQ ID NO: 31, and the monoclonal antibody binds specifically to sFlt1 variant 14 (sFlt1-14).

In certain embodiments, a monoclonal antibody, or antigen binding fragment, comprises the heavy chain variable domain sequence of SEQ ID NO: 1. In certain embodiments, the monoclonal antibody, or antigen binding fragment, comprises the light chain variable domain sequence of SEQ ID NO: 9. In certain embodiments, a monoclonal antibody, or antigen binding fragment, comprises the heavy chain variable domain sequence of SEQ ID NO: 1 and the light chain variable domain sequence of SEQ ID NO: 9. In certain embodiments, a monoclonal antibody, or antigen binding fragment, comprises the heavy chain variable domain sequence of SEQ ID NO: 17. In certain embodiments, a monoclonal antibody, or antigen binding fragment, comprises the light chain variable domain sequence of SEQ ID NO: 25. In certain embodiments, a monoclonal antibody, or antigen binding fragment, comprises the heavy chain variable domain sequence of SEQ ID NO: 17 and the light chain variable domain sequence of SEQ ID NO: 25.

In some embodiments, a monoclonal antibody, or antigen binding fragment, is a humanized antibody, a diabody, a chimeric antibody, a Fab fragment, a F(ab')2 fragment, or an Fv fragment. In some embodiments, a monoclonal antibody, or antigen binding fragment, comprises a heavy chain constant domain selected from the group consisting of IgG, IgG1, IgG2, IgG2A, IgG2B, IgG2C, IgG3, IgG4, IgA1, IgA2, IgD, IgM, and IgE constant domains. In some embodiments, a monoclonal antibody, or antigen binding fragment, is conjugated to an agent selected from the group consisting of a fluorescent agent, a luminescent agent, an enzymatic agent and a radioactive agent.

Further aspects of the disclosure relate to isolated nucleic acids encoding a protein comprising three complementarity determining regions (CDRs): CDRH1, CDRH2, and CDRH3. In some embodiments, CDRH3 comprises a sequence as set forth in SEQ ID NO: 7 or 23. In some embodiments, CDRH1 comprises a sequence as set forth in SEQ ID NO: 3 or 19. In some embodiments, CDRH2 comprises a sequence as set forth in SEQ ID NO: 5 or 21.

Further aspects of the disclosure relate to isolated nucleic acids encoding a protein comprising three complementarity determining regions (CDRs): CDRL1, CDRL2, and CDRL3. In some embodiments, CDRL3 comprises a sequence as set forth in SEQ ID NO: 15 or 31. In some embodiments, CDRL1 comprises a sequence as set forth in SEQ ID NO: 11 or 27. In some embodiments, CDRL2 comprises a sequence as set forth in SEQ ID NO: 13 or 29.

Further aspects of the disclosure relate to isolated nucleic acids comprising a sequence as set forth in SEQ ID NO: 2, 4, 6, 8, 10, 12, 14, 16, 18, 20, 22, 24, 26, 28, 30, or 32. In some embodiments, isolated cells are provided that comprise an isolated nucleic acid disclosed herein.

According to other aspects of the disclosure, methods are provided for assessing a biological sample obtained from a pregnant subject (e.g., for purposes of evaluating preeclampsia status in the subject). In some embodiments, such methods involve (a) preparing an immunological reaction mixture that comprises protein of a biological sample obtained from the pregnant subject and an isoform-specific antibody or antigen binding fragment that binds soluble Flt1 (sFlt1) protein; (b) maintaining the immunological reaction mixture under conditions that permit binding complexes to form between the antibody or antigen binding fragment and a sFlt1 protein isoform; and (c) determining the extent of binding complex formation. In some embodiments, the subject is a pregnant human subject, and the method further comprises repeating steps (a)-(c) one or more times during the subject's pregnancy. In some embodiments, the subject is a pregnant human subject, and the method further comprises repeating steps (a)-(c) up to 2, up to 3, up to 4, up to 5, up to 6, up to 7, up to 8, up to 9, up to 10 times or more during the subject's pregnancy.

In some embodiments, the subject is a pregnant human subject at a gestational week in the range of 21 to 27 weeks. In some embodiments, the subject is a pregnant human subject at a gestational week in the range of 28 to 32 weeks. In some embodiments, the subject is a pregnant human subject at a gestational week up to 21 weeks. In some embodiments, the subject has a risk factor for preeclampsia.

In some embodiments, the risk factor is hypertension. In some embodiments, the risk factor is diabetes. In some embodiments, the diabetes is diabetes mellitus or gestational diabetes. In some embodiments, the subject is at low risk for preeclampsia. In some embodiments, the biological sample is whole blood, serum or plasma sample.

In some embodiments, the antibody or antigen binding fragment is immobilized to a solid support. In some embodiments, the antibody or antigen binding fragment is detectably labeled. In some embodiments, the antibody or antigen binding fragment binds an amino acid sequence set forth as: EHCNKKAVFSRISKFKSTRNDCTTQSNVKH (SEQ ID NO: 38). In some embodiments, the antibody or antigen binding fragment binds an amino acid sequence set forth as: CNKKAVFSRISKFKSTRN (SEQ ID NO: 43). In some embodiments, the antibody or antigen binding fragment binds variant 1 of sFlt1 (sFlt1-1) with a KD of less than 10-7 M. In some embodiments, the antibody or antigen binding fragment binds an amino acid sequence set forth as: DQEAPYLLRNLSDHTVAISSSTTLDCHANGVPEPQIT-WFKNNHKIQQEP (SEQ ID NO: 40). In some embodiments, the antibody or antigen binding fragment binds an amino acid sequence set forth as: CDQEAPYLLRNLSDH (SEQ ID NO: 42). In some embodiments, the antibody or antigen binding fragment binds variant 14 of sFlt1 (sFlt1-14) with a KD of less than 10-7 M. In some embodiments, the antibody or antigen binding fragment is a monoclonal antibody.

BRIEF DESCRIPTION OF THE DRAWINGS

FIGS. 1A-1B is a representation of the alignment of c-terminal peptide sequences used for generation of mouse mAbs specific to sFlt1-14 (dashed box) and sFlt1-1 (solid box) and peptide sequences used for screening ELISAs for sFlt1-14-specific mAbs (dashed line) and sFlt1-specific mAbs (solid line). In FIG. 1A, a keyhole limpet hemocyanin (KLH) fusion protein was chemically linked to an N-terminal Cys residue on each sFlt peptide antigen used for immunizations or a Thioredoxin (TRX) or glutathione S-transferase (GST) fusion protein tagged was expressed upstream and in-frame with a sFlt1-14-specific peptide (TRX-Exon14) or sFlt1-specific peptide (GST-1C), respectively, used for screening ELISAs. Full-length sFlt1-1 containing a C-terminal His tag was used to generate all other mouse mAbs and HuMAbs that recognize total sFlt1. Full-length sFlt1-14 and sFlt1-1 are shown with the various domains labeled 1 through 7 (sFlt1-14 contains a partial domain 7, or exon 14) and unique c-terminal tails. Partial sFlt1-14 and sFlt1-1 c-terminal amino acid sequences (residues 651-706) are displayed with arrows indicating their general region within the protein. In FIG. 1A SEQ ID NOs: 42, 40, 43, and 38 appear from top to bottom, respectively. FIG. 1B is a schematic of sFlt1-14 and sFlt1-1 proteins identifying the unique epitopes antibodies were directed against. In FIG. 1B SEQ ID NOs: 44 and 45 appear from top to bottom, respectively.

FIGS. 2A-2B demonstrate hybridoma cultures screened by ELISA against (FIG. 2A) GST-1C or (FIG. 2B) TRX-Exon14 to isolate sFlt1-1 or sFlt1-14 specific mAbs, respectively. 1CKLH18 and Ex14-1 were selected for their favorable binding properties as isoform-specific mAbs, while the total sFlt1-specific mAb, 10 ugR#9, which binds a more N-terminal region of the full length protein, was included as a negative control.

FIGS. 3A-3C are representations of mouse mAbs EX14-1 (FIG. 3A) and 1C-KLH-18 (FIG. 3B) specifically detecting their respective endogenous sFlt isoforms in amniotic fluid on a western blot. Each mAb recognizes a single protein of the expected molecular weight (~115 kDa) when compared to recombinant standards and only detects its appropriate recombinant standard. A human VEGFR1-specific mouse mAb that binds an epitope in common with total sFlt (Sigma Cat.# V4262) is included as a positive control (C) and appropriately detects both sFlt recombinant standards in addition to sFlt in amniotic fluid.

FIGS. 4A-4E show mouse mAbs specific for sFlt splice variants as measured by capture ELISA. Total sFlt-specific mAb, 10 ugR#9, recognizes both recombinant sFlt1-1 (FIG. 4A) and sFlt1-14 (FIG. 4B) splice variants with similar sensitivity. However, sFlt1-specific mAb, 1C-KLH-18, only detects sFlt1-1 (FIG. 4A) while sFlt1-14-specific mAb, EX14-1, only detects sFlt1-14 (FIG. 4B). In addition, each mAb specifically recognizes endogenous sFlt present in biological fluid (amniotic fluid; FIG. 4C), while fluid that contains very low levels of sFlt (normal human sera; FIG. 4D) is not detected. To assess interference of quantitation in biological fluids (FIG. 4E), where 25 ng/mL of recombinant sFlt1-14 was spiked into normal human sera or amniotic fluid.

FIG. 6 is a representation of the amino acid and nucleic acid sequences of the VH chain expressed by clone 1C-KLH-18. The V-segment, D-segment and J-segment genes are listed above the amino acid and nucleic acid sequences. The CDRs identified by the Kabat method are overlined.

FIG. 7 is a representation of the amino acid and nucleic acid sequences of the VK chain expressed by clone 1C-KLH-18. The V-segment and J-segment genes are listed above the amino acid and nucleic acid sequences. The CDRs identified by the Kabat method are overlined.

FIG. 8 is a representation of the amino acid and nucleic acid sequences of the VH chain expressed by clone EX14-1. The V-segment, D-segment and J-segment genes are listed above the amino acid and nucleic acid sequences. The CDRs identified by the Kabat method are overlined.

FIG. 9 is a representation of the amino acid and nucleic acid sequences of the VK chain expressed by clone EX14-1. The V-segment and J-segment genes are listed above the amino acid and nucleic acid sequences. The CDRs identified by the Kabat method are overlined.

FIGS. 10A-10F show sFlt1 isoform and VEGFR-1 quantitation from serum samples at three gestational windows (GW) during pregnancy. (FIG. 10A) sFlt1-1, (FIG. 10B) sFlt1-14 and (FIG. 10C) VEGFR-1 levels from all women included in the study and (FIGS. 10D-10F, respectively) a subset from women included in FIGS. 10A-10C diagnosed with chronic hypertension and/or diabetes mellitus (chtn_dm) are reported as the mean biomarker level+/− SEM. *p≤0.05; **p≤0.01.

DETAILED DESCRIPTION

Figure 5:
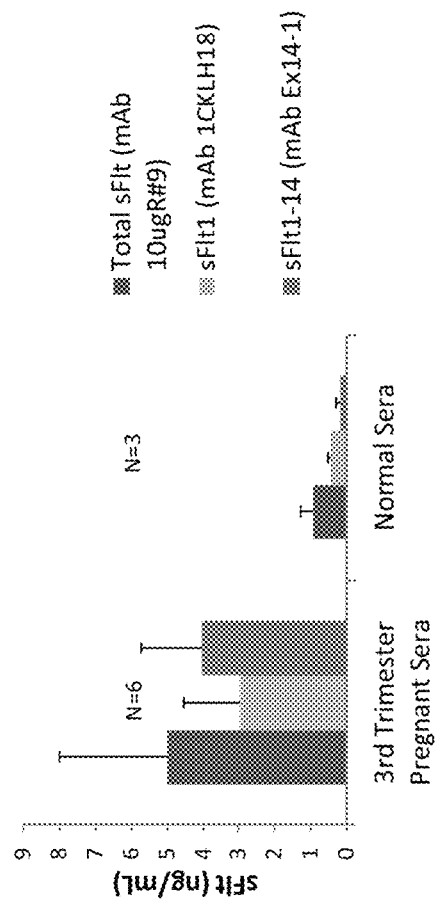
FIG. 5 is a representation of mAbs specific for total sFlt (10 ugR#9) and splice variants sFlt1-1 (1C-KLH-18) and sFlt1-14 (EX14-1) recognizing their respective proteins in healthy 3$^{rd}$ trimester pregnant sera as compared to normal, non-pregnant control sera. sFlt levels rise during the 3$^{rd}$ trimester of most pregnancies and, as expected, a wide range of values were obtained (1.15-19.93 ng/mL for total sFlt in pregnancy cohort vs. 0.53-1.61 ng/mL in controls). Values are reported as the average with standard error. Sample size is indicated in the graphic.

Aspects of the present disclosure relate to a recognition that elevated levels of sFlt1-1 and/or sFlt1-14 (isoforms of soluble Flt1 resulting from alternative splicing) are implicated as both a sign and pathophysiological cause of preeclampsia. However, suitable methods to measure or detect changes in physiological levels of sFlt1-1 and/or sFlt1-14 have been lacking. Binding agents (e.g., antibodies and antigen binding fragments) disclosed herein are sufficiently specific and sensitive to distinguish between sFlt1-1 and sFlt1-14. Such binding agents measure physiological concentrations of sFlt1-1 and sFlt1-14 with a specificity and sensitivity that is useful for the general clinical management of pregnant patients or candidates for therapies intended to ameliorate dysfunctions related to sFlt1-1 and/or sFlt1-14 levels. Accordingly, aspects of the disclosure relate to antibodies and antigen binding fragments that bind specifically to sFlt1-1 and/or sFlt1-14. In addition, antibodies and antigen binding fragments are provided that can be used in assays to distinguish between sFlt1-1 and sFlt1-14. It has been further discovered that these binding agents can be used in assays with high sensitivity, facilitating low thresholds of quantitation and detection. Examples of these binding agents are provided that demonstrate properties useful for the development and implementation of assays that can assist in the diagnosis and management of preeclampsia and related conditions.

A large change in circulating concentrations of sFlt1 proteins can be detected prior to clinically evident disease, and measurement of specific sFlt1 protein isoforms over time is useful to predict the development of preeclampsia. sFlt1 protein isoforms may be especially useful biomarkers for pregnant women with risk factors, such as chronic hypertension and/or diabetes co-morbidities. This further suggests that measurement of specific sFlt isoforms, individually or as a ratio or other multivariate measurement, and/or the measurement through time or in different tissues or fluids can provide improved methods to diagnose, predict or predict the timing and/or severity of preeclampsia or eclampsia in which the ability to accurately quantitate sFlt isoforms including but not limited to sFlt1-1 or sFlt1-14 will provide a useful addition to research, diagnostic and prognostic tools. Currently there are no clinically useful tests available that provide appropriate sensitivity or specificity to predict the risk of preeclampsia, time to onset, progression or ultimate severity. The present disclosure, therefore, addresses a need for methods to specifically and sensitively measure physiological levels of sFlt and its isoforms, sFlt1-1 and sFlt1-14, and for reagents that can be used readily and consistently in the execution of such methods in a clinical or clinical research setting.

Preeclampsia is a dangerous medical condition impacting many pregnant women and their fetuses. Preeclampsia is a multi-system disorder characterized by the new onset of hypertension and proteinuria after 20 weeks of gestation and is estimated to affect 3%-8% of pregnancies. Cases may demonstrate severe features, which include systolic blood pressure >160 mm Hg or diastolic blood pressure >110 mmHg on two occasions at least 4 hours apart, thrombocytopenia with platelet count <100,000/ml, impaired liver function with liver enzymes twice normal, progressive renal insufficiency with serum creatinine >1.1 mg/dl and/or evidence of central nervous system dysfunction (new onset cerebral or visual disturbances), persistent severe right upper quadrant or epigastric pain, or pulmonary edema. It is estimated that eclampsia, the development of grand mal seizures in a woman with preeclampsia, develops in 1-2% of women with preeclampsia.

In the United States, preeclampsia/eclampsia is one of the leading causes of maternal death, while globally 10 to 15 percent of maternal deaths related directly to obstetric complications are associated with preeclampsia/eclampsia. Several risk factors for preeclampsia have been identified, including occurrence and severity of preeclampsia in previous pregnancies, family history, nulliparity, advanced maternal age, multiple gestations and pre-existing medical conditions such as diabetes and high blood pressure. For women with chronic hypertension and/or pre-existing renal disease, superimposed preeclampsia may be difficult to diagnose. Both diagnosis and management of preeclampsia can be challenging in such cases. Management options of the condition are limited, and therapeutic options are limited to delivery of the fetus, sometimes significantly pre-term.

The current definitive treatment of preeclampsia is delivery to prevent development of maternal or fetal complications from disease progression and the decision to so treat is based upon gestational age, the severity of preeclampsia, and maternal and fetal condition. Patients near term are delivered; however, remote from term, the risks of serious sequelae from disease progression need to be weighed against the risks of preterm birth. When mother and fetus are stable, a conservative approach is warranted, but tests may be less than completely reassuring and prognostic precision is weak, making it useful to monitor patients frequently and in some cases leading to early admission for more comprehensive monitoring and to facilitate intervention should it become useful.

In some cases, prediction of preeclampsia is of limited benefit because current therapies, excepting delivery of the fetus and placenta, do not impact the development of the disorder, the speed of development, nor its ultimate severity. However, the sensitive and specific early identification of women at risk promotes informed patient choice and appropriate management by clinicians, which maximize the chances of optimal maternal and fetal outcomes, during pregnancy, perinatally and potentially post-partum. In addition, recent developments in the understanding of an underlying pathophysiological mechanism appear to have improved the general understanding of the molecular basis of preeclampsia and related conditions and this research, which hinges on the observation that preeclampsia is caused by dysregulation of angiostatic processes, and specifically that an excess of soluble fms-like tyrosine kinase (sFlt) present in preeclamptics serves as a sink for vascular endothelial growth factor (VEGF) thus preventing VEGF from binding to, and inducing the activity of cell surface receptors (such as Flt-1) promoting the mitogenesis of endothelial cells. Regulation of such signaling pathways appears to be important to the appropriate angiogenesis of the developing placenta which provides an adaptive explanation for the role of sFlt in normal pregnancy. It also suggests how an excess of the molecule might result in abnormal development of the placenta as well as impacting other organs where the maintenance and regulation of endothelial barriers is important, such as the glomerular capillaries in the kidneys, where dysregulation of the fenestrated endothelium can result in the passage of proteins into the urine. The understanding of these mechanisms had opened the door to the proposal of a number of therapeutic modalities to address such imbalances in angiogenic factors. However, therapeutic interventions may carry the risk of themselves contributing to dysregulation of the angiogenic balance during pregnancy and the measurement of the concentration of the sFlt, the rate of change and prediction of the likely development of the onset, course and severity of symptoms will be important to the proper evaluation and management of patients considered for novel interventions addressing this pathway. In addition the ability to accurately and precisely quantitate sFlt will also promote the development and testing of such proposed therapies.

Antibodies that Bind sFlt Isoforms

The present disclosure provides antibodies and antigen binding fragments that bind to sFlt isoforms, including sFlt1-1 and sFlt1-14. The monoclonal antibodies of the disclosure may be murine or chimeric or in other forms. A detailed description of the antibodies of the disclosure as well as methods for the production and identification of the antibodies of the disclosure is provided herein.

In some embodiments, antibodies, also known as immunoglobulins, are tetrameric glycosylated proteins composed of two light (L) chains of approximately 25 kDa each and two heavy (H) chains of approximately 50 kDa each. Two types of light chain, termed lambda and kappa, may be found in antibodies. Depending on the amino acid sequence of the constant domain of heavy chains, immunoglobulins can be assigned to five major classes: A, D, E, G, and M, and several of these may be further divided into subclasses (isotypes), e.g., $IgG_1$, $IgG_2$, $IgG_3$, $IgG_4$, $IgA_1$, and $IgA_2$. Each light chain typically includes an N-terminal variable (V) domain ($V_L$) and a constant (C) domain ($C_L$). Each heavy chain typically includes an N-terminal V domain ($V_H$), three or four C domains ($C_H$1-3), and a hinge region. The $C_H$ domain most proximal to $V_H$ is designated as $C_H1$. The $V_H$ and $V_L$ domains consist of four regions of relatively conserved sequences called framework regions (FR1, FR2, FR3, and FR4), which form a scaffold for three regions of hypervariable sequences (complementarity determining regions, CDRs). The CDRs contain most of the residues responsible for specific interactions of the antibody with the antigen. CDRs are referred to as CDR1, CDR2, and CDR3. Accordingly, CDR constituents on the heavy chain are referred to as CDRH1, CDRH2, and CDRH3, while CDR constituents on the light chain are referred to as CDRL1, CDRL2, and CDRL3. The CDRs typically refer to the Kabat CDRs, as described in Sequences of Proteins of Immunological Interest, US Department of Health and Human Services (1991), eds. Kabat et al. Another standard for characterizing the antigen binding site is to refer to the hypervariable loops as described by Chothia. See, e.g., Chothia, D. et al. (1992) J. Mol. Biol. 227:799-817; and Tomlinson et al. (1995) EMBO J. 14:4628-4638. Still another standard is the AbM definition used by Oxford Molecular's AbM antibody modeling software. See, generally, e.g., Protein Sequence and Structure Analysis of Antibody Variable Domains. In: Antibody Engineering Lab Manual (Ed.: Duebel, S, and Kontermann, R., Springer-Verlag, Heidelberg). Embodiments described with respect to Kabat CDRs can alternatively be implemented using similar described relationships with respect to Chothia hypervariable loops or to the AbM-defined loops, or combinations of any of these methods.

In some embodiments, anti-sFlt1-1 and anti-sFlt1-14 antibodies of the present disclosure and the nucleic acid molecules of the present disclosure that encode the antibodies include the CDR amino acid and nucleic acid sequences shown in Table 1 below and in FIGS. 6-9.

TABLE 1

| Antibody | CDRH1 | CDRH2 | CDRH3 | CDRL1 | CDRL2 | CDRL3 |
|---|---|---|---|---|---|---|
| 1C-KLH-18 | | | | | | |
| Amino acid: | (SEQ ID NO: 3) | (SEQ ID NO: 5) | (SEQ ID NO: 7) | (SEQ ID NO: 11) | (SEQ ID NO: 13) | (SEQ ID NO: 15) |
| Nuc. Acid: | (SEQ ID NO: 4) | (SEQ ID NO: 6) | (SEQ ID NO: 8) | (SEQ ID NO: 12) | (SEQ ID NO: 14) | (SEQ ID NO: 16) |
| EX14-1 | | | | | | |
| Amino acid: | (SEQ ID NO: 19) | (SEQ ID NO: 21) | (SEQ ID NO: 23) | (SEQ ID NO: 27) | (SEQ ID NO: 29) | (SEQ ID NO: 31) |
| Nuc. Acid: | (SEQ ID NO: 20) | (SEQ ID NO: 22) | (SEQ ID NO: 24) | (SEQ ID NO: 28) | (SEQ ID NO: 30) | (SEQ ID NO: 32) |

In some embodiments, anti-sFlt1-1 and anti-sFlt1-14 binding agents of the disclosure include any antibody or antigen binding fragment that includes a CDRH1, CDRH2, CDRH3, CDRL1, CDRL2, or CDRL3, or combinations thereof, as provided for any one of the antibodies shown in Table 1 or FIGS. 7-9. In some embodiments, anti-sFlt1-1 and anti-sFlt1-14 binding agents include the CDRH1, CDRH2, CDRH3, CDRL1, CDRL2, and CDRL3 of any one of the antibodies shown in Table 1. The disclosure also includes any nucleic acid sequence that encodes a CDRH1, CDRH2, CDRH3, CDRL1, CDRL2, or CDRL3 as provided for any one of the antibodies shown in Table 1 or FIGS. 7-9. In some embodiments, the nucleic acids include the CDRH1, CDRH2, CDRH3, CDRL1, CDRL2, and CDRL3 nucleic acid sequences of any one of the antibodies shown in Table 1. Antibody heavy and light chain CDR3 domains may play a particularly important role in the binding specificity/affinity of an antibody for an antigen. Accordingly, the anti-sFlt1-1 and anti-sFlt1-14 binding agents of the disclosure, or the nucleic acid molecules thereof, may include at least the heavy and/or light chain CDR3s of antibodies as shown in Table 1 or FIGS. 6-9.

The complete amino acid and nucleic acid sequences for the heavy chain variable region and light chain variable region of the antibodies listed in Table 1 are provided in Table 2 and in FIGS. 6-9.

TABLE 2

| Antibody | Heavy Chain Variable Region | Light Chain Variable Region |
|---|---|---|
| 1C-KLH-18 | | |
| Amino acid: | SEQ ID NO: 1 | SEQ ID NO: 9 |
| Nuc. Acid: | SEQ ID NO: 2 | SEQ ID NO: 10 |
| EX14-1 | | |
| Amino acid: | SEQ ID NO: 17 | SEQ ID NO: 25 |
| Nuc. Acid: | SEQ ID NO: 18 | SEQ ID NO: 26 |

In some embodiments, anti-sFlt1-1 and anti-sFlt1-14 antibodies of the disclosure include any antibody that includes a heavy chain variable domain or a light chain variable domain or both as shown in Table 2 or FIGS. 6-9. The disclosure also includes any nucleic acid molecule encoding an antibody that includes a heavy chain variable domain or a light chain variable domain nucleic acid sequence, or both, as shown in Table 2 or FIGS. 6-9.

Anti-sFlt1-1 and anti-sFlt1-14 binding agents of this disclosure may optionally comprise antibody constant regions or parts thereof. For example, a $V_L$ domain may be attached at its C-terminal end to a light chain constant domain like Cκ or Cλ. Similarly, a $V_H$ domain or portion thereof may be attached to all or part of a heavy chain like IgA, IgD, IgE, IgG, and IgM, and any isotype subclass.

Antibodies may include suitable constant regions (see, for example, Kabat et al., Sequences of Proteins of Immunological Interest, No. 91-3242, National Institutes of Health Publications, Bethesda, Md. (1991)). Therefore, antibodies within the scope of this may disclosure include $V_H$ and $V_L$ domains, or an antigen binding portion thereof, combined with constant regions known in the art.

In certain embodiments, the $V_H$ and/or $V_L$ domains may be reverted to germline sequence, e.g., the FR of these domains are mutated using conventional molecular biology techniques to match those produced by the germline cells. In other embodiments, the FR sequences remain diverged from the consensus germline sequences.

In some embodiments, anti-sFlt1-1 and anti-sFlt1-14 antibodies or antigen binding fragments may or may not include the framework region of the antibodies shown in FIGS. 6-9. In some embodiments, anti-sFlt1-1 and anti-sFlt1-14 antibodies are murine antibodies and include the variable region sequences shown in FIGS. 6-9.

In some embodiments, an anti-sFlt1-1 binding agent of the disclosure can bind to sFlt1-1 with high affinity, e.g., with a Kd less than $10^{-7}$ M, $10^{-8}$ M, $10^{-9}$ M, $10^{-10}$ M, $10^{-11}$ M or lower. For example, anti-sFlt1-1 antibodies or antigen binding fragments thereof can bind to sFlt1-1 with an affinity between 5 pM and 500 nM, e.g., between 50 pM and 100 nM, e.g., between 500 pM and 50 nM. The disclosure also includes antibodies or antigen binding fragments that compete with any of the antibodies described herein for binding to sFlt1-1 and that have an affinity of 50 nM or lower (e.g., 20 nM or lower, 10 nM or lower, 500 pM or lower, 50 pM or lower, or 5 pM or lower). The affinity and binding kinetics of the anti-sFlt1-1 antibody can be tested using any method known in the art including but not limited to biosensor technology (e.g., OCTET or BIACORE).

In some embodiments, an anti-sFlt1-14 binding agent of the disclosure can bind to sFlt1-14 with high affinity, e.g., with a Kd less than $10^{-7}$ M, $10^{-8}$ M, $10^{-9}$ M, $10^{-10}$ M, $10^{-11}$ M or lower. For example, anti-sFlt1-14 antibodies or antigen binding fragments thereof can bind to sFlt1-14 with an affinity between 5 pM and 500 nM, e.g., between 50 pM and 100 nM, e.g., between 500 pM and 50 nM. The disclosure also includes antibodies or antigen binding fragments that compete with any of the antibodies described herein for binding to sFlt1-14 and that have an affinity of 50 nM or lower (e.g., 20 nM or lower, 10 nM or lower, 500 pM or lower, 50 pM or lower, or 5 pM or lower). In yet another embodiment, the anti-sFlt1-14 antibodies have dissociation kinetics in the range of 0.5-20 nM. The affinity and binding kinetics of the anti-sFlt1-14 antibody can be tested using any method known in the art including but not limited to biosensor technology (e.g., OCTET or BIACORE). The anti-sFlt1-14 antibody of the disclosure does not bind to sFlt1.

In some embodiments, antibodies or antigen binding fragments are provided that bind with relatively high affinity to sFlt1-1 but do not substantially bind to sFlt1-14. In some embodiments, antibodies or antigen binding fragments are provided that bind with relatively high affinity to sFlt1-14 but do not substantially bind to sFlt1-1. However, in some embodiments, antibodies or antigen binding fragments are provided that bind with relatively high affinity to both sFlt1-1 and sFlt1-14.

As used herein, the term "antibody" generally refers to an immunoglobulin. All derivatives thereof which maintain or possess specific binding ability are also provided herein. An antibody preparation may be monoclonal or polyclonal.

As used herein, the term "antibody fragment" or "antigen binding fragment" refers to any derivative of an antibody which is less than full-length. Generally, an antigen binding fragment retains at least a significant portion of the full-length antibody's specific binding ability. Examples of antigen binding fragments include, but are not limited to, Fab, Fab', F(ab')2, scFv, Fv, dsFv diabody, and Fd fragments. Antigen binding fragments may be produced by any appropriate means. For instance, an antigen binding fragment may be enzymatically or chemically produced by fragmentation of an intact antibody or it may be recombinantly produced from a gene encoding the partial antibody sequence. Alternatively, an antigen binding fragment may be wholly or partially synthetically produced. An antigen binding fragment may optionally be a single chain antibody fragment. Alternatively, a fragment may comprise multiple chains which are linked together, for instance, by disulfide linkages. An antigen binding fragment may also optionally be a multimolecular complex. A functional antigen binding fragment will typically comprise at least about 50 amino acids and more typically will comprise at least about 200 amino acids.

Single-chain Fvs (scFvs) are recombinant antigen binding fragments consisting of only the variable light chain (VL) and variable heavy chain (VH) covalently connected to one another by a polypeptide linker. Either VL or VH may be the NH2-terminal domain. The polypeptide linker may be of variable length and composition so long as the two variable domains are bridged without serious steric interference. Typically, the linkers are comprised primarily of stretches of glycine and serine residues with some glutamic acid or lysine residues interspersed for solubility.

Diabodies are dimeric scFvs. The components of diabodies typically have shorter peptide linkers than most scFvs, and they show a preference for associating as dimers.

A Fv fragment is an antigen binding fragment which consists of one VH and one VL domain held together by noncovalent interactions. The term dsFv is used herein to refer to an Fv with an engineered intermolecular disulfide bond to stabilize the VH-VL pair.

A F(ab')2 fragment is an antigen binding fragment essentially equivalent to that obtained from immunoglobulins (typically IgG) by digestion with an enzyme pepsin at pH 4.0-4.5. The fragment may be recombinantly produced.

A Fab fragment is an antigen binding fragment essentially equivalent to that obtained by reduction of the disulfide bridge or bridges joining the two heavy chain pieces in the F(ab')2 fragment. The Fab' fragment may be recombinantly produced.

A Fab fragment is an antigen binding fragment essentially equivalent to that obtained by digestion of immunoglobulins (typically IgG) with the enzyme papain. The Fab fragment may be recombinantly produced. The heavy chain segment of the Fab fragment is the Fd piece.

Production of Antibodies that Bind sFlt, sFlt1-1, and sFlt1-14

Numerous methods may be used for obtaining antibodies, or antigen binding fragments thereof, of the disclosure. For example, antibodies can be produced using recombinant DNA methods. Monoclonal antibodies may also be produced by generation of hybridomas (see e.g., Kohler and Milstein (1975) Nature, 256: 495-499) in accordance with known methods. Hybridomas formed in this manner are then screened using standard methods, such as enzyme-linked immunosorbent assay (ELISA) and surface plasmon resonance (e.g., OCTET or BIACORE) analysis, to identify one or more hybridomas that produce an antibody that specifically binds with a specified antigen. Any form of the specified antigen may be used as the immunogen, e.g., recombinant antigen, naturally occurring forms, any variants or fragments thereof, as well as antigenic peptide thereof (e.g., any of the epitopes described herein as a linear epitope or within a scaffold as a conformational epitope). One exemplary method of making antibodies includes screening protein expression libraries that express antibodies or fragments thereof (e.g., scFv), e.g., phage or ribosome display libraries. Phage display is described, for example, in Ladner et al., U.S. Pat. No. 5,223,409; Smith (1985) Science 228: 1315-1317; Clackson et al. (1991) Nature, 352: 624-628; Marks et al. (1991) J. Mol. Biol., 222: 581-597WO92/18619; WO 91/17271; WO 92/20791; WO 92/15679; WO 93/01288; WO 92/01047; WO 92/09690; and WO 90/02809.

In addition to the use of display libraries, the specified antigen (e.g., sFlt1-1 or sFlt1-14) can be used to immunize a non-human animal, e.g., a rodent, e.g., a mouse, hamster, or rat. In one embodiment, the non-human animal is a mouse.

In another embodiment, a monoclonal antibody is obtained from the non-human animal, and then modified, e.g., chimeric, using recombinant DNA techniques known in the art. A variety of approaches for making chimeric antibodies have been described. See e.g., Morrison et al., Proc. Natl. Acad. Sci. U.S.A. 81:6851, 1985; Takeda et al., Nature 314:452, 1985, Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 2177096B.

For additional antibody production techniques, see Antibodies: A Laboratory Manual, eds. Harlow et al., Cold Spring Harbor Laboratory, 1988. The present disclosure is not necessarily limited to any particular source, method of production, or other special characteristics of an antibody.

Some aspects of the present invention relate to host cells transformed with a polynucleotide or vector. Host cells may be a prokaryotic or eukaryotic cell. The polynucleotide or vector which is present in the host cell may either be integrated into the genome of the host cell or it may be maintained extrachromosomally. The host cell can be any prokaryotic or eukaryotic cell, such as a bacterial, insect, fungal, plant, animal or human cell. In some embodiments, fungal cells are, for example, those of the genus *Saccharomyces*, in particular those of the species *S. cerevisiae*. The term "prokaryotic" includes all bacteria which can be transformed or transfected with a DNA or RNA molecules for the expression of an antibody or the corresponding immunoglobulin chains. Prokaryotic hosts may include gram negative as well as gram positive bacteria such as, for example, *E. coli, S. typhimurium, Serratia marcescens* and *Bacillus subtilis*. The term "eukaryotic" includes yeast, higher plants, insects and vertebrate cells, e.g., mammalian cells, such as NSO and CHO cells. Depending upon the host employed in a recombinant production procedure, the antibodies or immunoglobulin chains encoded by the polynucleotide may be glycosylated or may be non-glycosylated. Antibodies or the corresponding immunoglobulin chains may also include an initial methionine amino acid residue.

In some embodiments, once a vector has been incorporated into an appropriate host, the host may be maintained under conditions suitable for high level expression of the nucleotide sequences, and, as desired, the collection and purification of the immunoglobulin light chains, heavy chains, light/heavy chain dimers or intact antibodies, antigen binding fragments or other immunoglobulin forms may follow; see, Beychok, Cells of Immunoglobulin Synthesis, Academic Press, N.Y., (1979). Thus, polynucleotides or vectors are introduced into the cells which in turn produce the antibody or antigen binding fragments. Furthermore, transgenic animals, preferably mammals, comprising the aforementioned host cells may be used for the large scale production of the antibody or antibody fragments.

The transformed host cells can be grown in fermenters and cultured according to techniques known in the art to achieve optimal cell growth. Once expressed, the whole antibodies, their dimers, individual light and heavy chains, other immunoglobulin forms, or antigen binding fragments, can be purified according to standard procedures of the art, including ammonium sulfate precipitation, affinity columns, column chromatography, gel electrophoresis and the like; see, Scopes, "Protein Purification", Springer Verlag, N.Y. (1982). The antibody or antigen binding fragments can then be isolated from the growth medium, cellular lysates, or cellular membrane fractions. The isolation and purification of the, e.g., microbially expressed antibodies or antigen binding fragments may be by any conventional means such as, for example, preparative chromatographic separations and immunological separations such as those involving the use of monoclonal or polyclonal antibodies directed, e.g., against the constant region of the antibody.

Aspects of the disclosure relate to a hybridoma, which provides an indefinitely prolonged source of monoclonal antibodies. As an alternative to obtaining immunoglobulins directly from the culture of hybridomas, immortalized hybridoma cells can be used as a source of rearranged heavy chain and light chain loci for subsequent expression and/or genetic manipulation. Rearranged antibody genes can be reverse transcribed from appropriate mRNAs to produce cDNA. If desired, the heavy chain constant region can be exchanged for that of a different isotype or eliminated altogether. The variable regions can be linked to encode single chain Fv regions. Multiple Fv regions can be linked to confer binding ability to more than one target or chimeric heavy and light chain combinations can be employed. Any appropriate method may be used for cloning of antibody variable regions and generation of recombinant antibodies.

In some embodiments, an appropriate nucleic acid that encodes variable regions of a heavy and/or light chain is obtained and inserted into an expression vectors which can be transfected into standard recombinant host cells. A variety of such host cells may be used. In some embodiments, mammalian host cells may be advantageous for efficient processing and production. Typical mammalian cell lines useful for this purpose include CHO cells, 293 cells, or NSO cells. The production of the antibody or antigen binding fragment may be undertaken by culturing a modified recombinant host under culture conditions appropriate for the growth of the host cells and the expression of the coding sequences. The antibodies or antigen binding fragments may be recovered by isolating them from the culture. The expression systems may be designed to include signal peptides so that the resulting antibodies are secreted into the medium; however, intracellular production is also possible.

The disclosure also includes a polynucleotide encoding at least a variable region of an immunoglobulin chain of the antibodies described herein. In some embodiments, the variable region encoded by the polynucleotide comprises at least one complementarity determining region (CDR) of the VH and/or VL of the variable region of the antibody produced by any one of the above described hybridomas.

Polynucleotides encoding antibody or antigen binding fragments may be, e.g., DNA, cDNA, RNA or synthetically produced DNA or RNA or a recombinantly produced chimeric nucleic acid molecule comprising any of those polynucleotides either alone or in combination. In some embodiments, a polynucleotide is part of a vector. Such vectors may comprise further genes such as marker genes which allow for the selection of the vector in a suitable host cell and under suitable conditions.

In some embodiments, a polynucleotide is operatively linked to expression control sequences allowing expression in prokaryotic or eukaryotic cells. Expression of the polynucleotide comprises transcription of the polynucleotide into a translatable mRNA. Regulatory elements ensuring expression in eukaryotic cells, preferably mammalian cells, are well known to those skilled in the art. They may include regulatory sequences that facilitate initiation of transcription and optionally poly-A signals that facilitate termination of transcription and stabilization of the transcript. Additional regulatory elements may include transcriptional as well as translational enhancers, and/or naturally associated or heterologous promoter regions. Possible regulatory elements permitting expression in prokaryotic host cells include, e.g., the PL, Lac, Trp or Tac promoter in *E. coli*, and examples of regulatory elements permitting expression in eukaryotic host cells are the AOX1 or GAL1 promoter in yeast or the CMV-promoter, SV40-promoter, RSV-promoter (Rous sarcoma virus), CMV-enhancer, SV40-enhancer or a globin intron in mammalian and other animal cells.

Beside elements which are responsible for the initiation of transcription such regulatory elements may also include transcription termination signals, such as the SV40-poly-A site or the tk-poly-A site, downstream of the polynucleotide. Furthermore, depending on the expression system employed, leader sequences capable of directing the polypeptide to a cellular compartment or secreting it into the medium may be added to the coding sequence of the polynucleotide and are well known in the art. The leader sequence(s) is (are) assembled in appropriate phase with translation, initiation and termination sequences, and preferably, a leader sequence capable of directing secretion of translated protein, or a portion thereof, into, for example, the extracellular medium. Optionally, a heterologous polynucleotide sequence can be used that encode a fusion protein including a C- or N-terminal identification peptide imparting desired characteristics, e.g., stabilization or simplified purification of expressed recombinant product.

In some embodiments, polynucleotides encoding at least the variable domain of the light and/or heavy chain may encode the variable domains of both immunoglobulin chains or only one. Likewise, a polynucleotides may be under the control of the same promoter or may be separately controlled for expression. Furthermore, some aspects relate to vectors, particularly plasmids, cosmids, viruses and bacteriophages used conventionally in genetic engineering that comprise a polynucleotide encoding a variable domain of an immunoglobulin chain of an antibody or antigen binding fragment; optionally in combination with a polynucleotide that encodes the variable domain of the other immunoglobulin chain of the antibody.

In some embodiments, expression control sequences are provided as eukaryotic promoter systems in vectors capable of transforming or transfecting eukaryotic host cells, but control sequences for prokaryotic hosts may also be used. Expression vectors derived from viruses such as retroviruses, vaccinia virus, adeno-associated virus, herpes viruses, or bovine papilloma virus, may be used for delivery of the polynucleotides or vector into targeted cell population (e.g., to engineer a cell to express an antibody or antigen binding fragment). A variety of appropriate methods can be used to construct recombinant viral vectors. In some embodiments, polynucleotides and vectors can be reconstituted into liposomes for delivery to target cells. The vectors containing the polynucleotides (e.g., the heavy and/or light variable domain(s) of the immunoglobulin chains encoding sequences and expression control sequences) can be transferred into the host cell by suitable methods, which vary depending on the type of cellular host.

Modifications

Antibodies or antigen binding fragments of the disclosure may be modified with a detectable label, including, but not limited to, an enzyme, prosthetic group, fluorescent material, luminescent material, bioluminescent material, radioactive material, positron emitting metal, nonradioactive paramagnetic metal ion, and affinity label for detection and isolation of sFlt1-1 and/or sFlt1-14. The detectable substance may be coupled or conjugated either directly to the polypeptides of the disclosure or indirectly, through an intermediate (such as, for example, a linker known in the art) using techniques known in the art. Non-limiting examples of suitable enzymes include horseradish peroxidase, alkaline phosphatase, β-galactosidase, glucose oxidase, or acetylcholinesterase; non-limiting examples of suitable prosthetic group complexes include streptavidin/biotin and avidin/biotin; non-limiting examples of suitable fluorescent materials include biotin, umbelliferone, fluorescein, fluorescein isothiocyanate, rhodamine, dichlorotriazinylamine fluorescein, dansyl chloride, or phycoerythrin; an example of a luminescent material includes luminol; non-limiting examples of bioluminescent materials include luciferase, luciferin, and aequorin; and examples of suitable radioactive material include a radioactive metal ion, e.g., alpha-emitters or other radioisotopes such as, for example, iodine ($^{131}$I, $^{125}$I, $^{123}$I, $^{121}$I), carbon ($^{14}$C), sulfur ($^{35}$S), tritium ($^{3}$H), indium ($^{115m}$In, $^{113m}$In, $^{112}$In, $^{111}$In) and technetium ($^{99}$Tc, $^{99m}$Tc), thallium ($^{201}$Ti), gallium ($^{68}$Ga, $^{67}$Ga), palladium ($^{103}$Pd) molybdenum ($^{99}$Mo), xenon ($^{133}$Xe), fluorine ($^{18}$F), $^{153}$Sm, Lu, $^{159}$Gd, $^{149}$Pm, $^{140}$La, $^{175}$Yb, $^{166}$Ho, $^{90}$Y, $^{47}$Sc, $^{86}$R, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, and tin ($^{113}$Sn, $^{117}$Sn).) The detectable substance may be coupled or conjugated either directly to the anti-sFlt1-1 and sFlt1-14 antibodies of the disclosure or indirectly, through an intermediate (such as, for example, a linker known in the art) using techniques known in the art. Anti-sFlt1-1 and anti-sFlt1-14 antibodies conjugated to a detectable substance may be used for diagnostic assays as described herein.

Applications

Antibodies or antigen binding fragments of the disclosure may be used in methods and kits for the diagnosis of preeclampsia or eclampsia, or prediction of the risk of developing preeclampsia or eclampsia, or for predicting the likely onset, course and/or severity of preeclampsia and generally to inform the clinical management of pregnancy and specifically preeclamptic subjects. For the diagnostic methods and compositions, an anti-sFlt1-1 antibody, or antigen binding fragment thereof, of the disclosure will bind to sFlt1-1 but not sFlt1-14 in a sample of biological fluids and or tissue from a subject and/or the fetus. In some embodiments, an anti-sFlt1-14 antibody, or antigen binding fragment thereof, will bind to sFlt1-14 but not sFlt1-1 in a sample of biological fluids and/or tissue from a subject and/or the fetus. In some embodiments, if sFlt1-1 and/or sFlt1-14 is detected using an antibody of the disclosure, or detected above a certain threshold in a univariate or multivariate comparison to reference samples and/or reference data, the subject may be diagnosed with preeclampsia or eclampsia or having an increased risk of developing preeclampsia or eclampsia. Similarly changes in the measurement of sFlt1-1 and/or sFlt1-14, directly or in a ratio or other multivariate measurement, or their differential distribution in different samples may have prognostic value, indicating the likely timing of onset, and/or the course or progression of the condition, and/or the likely ultimate severity or outcome.

Experience with the implementation of the methods enabled by the reagents disclosed in the disclosure will also inform the development of novel therapies for preeclampsia and provide a means of assuring the safety and efficacy with which such novel therapeutic agents may be used. The diagnostic methods and compositions can be used as an initial screen, a single test, or in conjunction with additional clinical and serological testing, used by a clinician in the diagnosis, prediction of preeclampsia or eclampsia and/or prognostically following diagnosis. In diagnostic, predictive and prognostic methods of the disclosure, the level of sFlt1-1 and/or sFlt1-14 detected in a subject sample may be compared to the level of sFlt1-1 and/or sFlt1-14 detected in a normal reference sample (e.g., a sample from a subject known not to have preeclampsia or not be at risk for developing preeclampsia) or the measured level of the sFlt1-1 and/or sFlt1-14 can be used in the calculation of a multivariate parameter that can be further used in comparison to reference samples or reference data. The relationship between the univariate or multivariate parameters measured for the subject's sample or samples in comparison with the reference data can support objective diagnosis or provide information relevant to the estimation of patient risk relating to the onset, course and severity of preeclampsia or eclampsia.

Diagnostic, predictive and prognostic methods and compositions can include the use of diagnostic assays known in the art including, but not limited to, immunoassays, enzyme-linked immunosorbent assays (ELISA), and fluorescence-linked immunosorbent assays (FLISA).

Thus, a further embodiment relates to a method for detecting a sFlt1 isoform in a sample obtained from a subject. The sample may be obtained from a pregnant subject at any appropriate time, e.g., at any appropriate gestational week. For example, the subject may be a pregnant woman at a gestational week up to 21 weeks. The subject may be a pregnant woman at a gestational week in the range of 21 to 27 weeks. The subject may be a pregnant woman at a gestational week in the range of 28 to 32 weeks. The subject may be a pregnant woman at a gestational week greater than 32 weeks. The subject may also have one or more risk factors for preeclampsia, including, for example, hypertension or diabetes, such as diabetes mellitus or gestational diabetes.

In some embodiments, a method for detecting a sFlt1 isoform in a sample obtained from a subject involve (a)

contacting the sample with the antibody or antigen binding fragment under conditions suitable for binding of the antibody or antigen binding fragment to the antigen, if the antigen is present in the sample, thereby forming binding complexes; and (b) determining the level of the antibody or antigen binding fragment bound to the antigen (e.g., determining the level of the binding complexes).

As used herein a binding complex refers to a biomolecular complex of antibody or antigen binding fragments bound to antigen (e.g., sFlt1-1 protein, sFlt1-14 protein). Binding complexes may comprise antibodies or antigen binding fragments with a single specificity or two or more antibodies or antigen binding fragments with different specificities. In one embodiment, a binding complex comprises two or more antibodies recognizing different antigenic sites on the same antigen. In some instances, an antibody or antigen binding fragment may be bound to an antigen, having bound to it other biomolecules such as RNA, DNA, polysaccharides or proteins. In one embodiment, a binding complex comprises two or more antibodies recognizing different antigens. In some embodiments, an antibody or antigen binding fragment in a binding complex (e.g., an immobilized antibody or antigen binding fragment bound to antigen), may itself by bound, as an antigen, to an antibody or antigen binding fragment (e.g., a detectably labeled antibody or antigen binding fragment). Thus, binding complexes may, in some instances, comprise multiple antigens and multiple antibodies or antigen binding fragments. Antigens present in binding complexes may or may not be in their native in situ conformation. In some embodiments, a binding complex is formed between an antibody or antigen binding fragment and a purified protein antigen, or isolated proteins comprising antigen, in which the antigen is not in its native in situ conformation. In some embodiments, a binding complex is formed between an antibody or antigen binding fragment and a purified protein antigen, in which the antigen is not in its native in situ conformation and is immobilized on solid support (e.g., a PVDF membrane). In some embodiments, a binding complex is formed with an antibody or antigen binding fragment and, for example, a cell surface protein that is present in situ in a native confirmation (e.g., on the surface of a cell). Antibodies or antigen binding fragments in binding complexes may or may not be detectably labeled. In some embodiments, binding complexes comprise detectably labeled antibodies or antigen binding fragments and non-labeled antibodies or antigen binding fragments. In some embodiments, binding complexes comprise detectably labeled antigen. In some embodiments, antibodies or antigen binding fragments, in binding complexes, are immobilized to one or more solid supports. In some embodiments, antigens, in binding complexes, are immobilized to one or more solid supports. Exemplary solid supports are disclosed herein and will be apparent to one of ordinary skill in the art. The foregoing examples of binding complexes are not intended to be limiting. Other examples of binding complexes will be apparent to one or ordinary skill in the art.

A further embodiment relates to a method for diagnosing a subject having, or at risk of having, preeclampsia, in which the method involves: (a) obtaining a biological sample from the subject and (b) determining the level of a sFlt1 isoform (e.g., sFlt1-1, sFlt1-14) in the biological sample using the antibody or antigen binding fragment.

In any of the detection, diagnosis, and monitoring methods, the antibody, or antigen binding fragments, or antigen may be conjugated to a solid support surface, either directly or indirectly. Methods for conjugation to solid supports are standard and can be accomplished via covalent and non-covalent interactions. Non-limiting examples of conjugation methods include: adsorption, cross-linking, protein A/G—antibody interactions, and streptavidin-biotin interactions. Other methods of conjugation will be readily apparent to one of ordinary skill in the art.

In some aspects, the foregoing detection, diagnosis, and monitoring methods include comparing the level of the antibody or antigen binding fragment bound to the antigen (e.g., binding complexes) to one or more reference standards. The reference standard may be, for example, the level of a corresponding sFlt1 isoform in a subject that does or does not have preeclampsia. In one embodiment, the reference standard is the level of sFlt1 isoform detected in a sample that does not contain sFlt1 isoform (e.g., a background level). Alternatively, a background level can be determined from a sample that contains a particular sFlt1 isoform, by contacting the sample with non-specific antibodies (e.g., antibodies obtained from non-immune serum). Then again, the reference standard may be the level of sFlt1 isoform detected in a sample that does contain sFlt1 isoform (e.g., a positive control). In some cases, the reference standard may be a series of levels associated with varying concentrations of sFlt1 isoform in a sample and useful for quantifying the concentration of sFlt1 isoform in the test sample. The foregoing examples of reference standards are not limiting and other suitable reference standard will be readily apparent to one of ordinary skill in the art.

A further embodiment relates to a method for monitoring preeclampsia in a subject having, or at risk of having, preeclampsia comprising: (a) obtaining a biological sample from the subject, (b) determining the level of a sFlt1 isoform in the biological sample using the antibody or antigen binding fragment, and (c) repeating steps (a) and (b) on one or more occasions (e.g., every one to four gestational weeks).

Another embodiment relates to a diagnostic composition comprising any one of the above described antibodies, antigen binding fragments, polynucleotides, vectors or cells and optionally suitable means for detection. The antibodies or antigen binding fragments are, for example, suited for use in immunoassays in which they can be utilized in liquid phase or bound to a solid phase carrier. Examples of immunoassays which can utilize the antibody or antigen binding fragments are competitive and non-competitive immunoassays in either a direct or indirect format. Examples of such immunoassays are the Enzyme Linked Immunoassay (ELISA), radioimmunoassay (RIA), the sandwich (immunometric assay), flow cytometry, the western blot assay, immunoprecipitation assays, immunohistochemistry, immuno-microscopy, lateral flow immuno-chromatographic assays, and proteomics arrays. The antigens and antibodies or antigen binding fragments can be bound to many different solid supports (e.g., carriers, membrane, columns, proteomics array, etc.). Examples of solid support materials include glass, polystyrene, polyvinyl chloride, polyvinylidene difluoride, polypropylene, polyethylene, polycarbonate, dextran, nylon, amyloses, natural and modified celluloses, such as nitrocellulose, polyacrylamides, agaroses, and magnetite. The nature of the support can be either fixed or suspended in a solution (e.g., beads).

By a further embodiment, antibodies and antigen binding fragments provided herein may also be used in a method for the diagnosis of preeclampsia in a subject by obtaining a biological sample from the subject which may be a blood sample or any other appropriate body fluid sample. The diagnostic procedure may comprise contacting the blood sample (whole blood, serum, plasma), or protein sample isolated therefrom, with an antibody, or antigen binding fragment, under conditions enabling the formation of binding complexes between antibody or antigen binding fragment and antigen. The level of such binding complexes may then be determined by methods known in the art. In some embodiments, a level of binding complexes significantly higher than that formed in an appropriate control sample indicates preeclampsia.

In some embodiments, the biological sample is contacted with the antibody or antigen binding fragment under conditions suitable for binding of the antibody or antigen binding fragment to a sFlt1 isoform, if the antigen is present in the sample, and formation of binding complexes consisting of antibody, or antigen binding fragment, bound to the antigen. This contacting step is typically performed in a reaction chamber, such as a tube, plate well, membrane bath, cell culture dish, microscope slide, and the like. In some embodiments, the antibody or antigen binding fragment is immobilized on a solid support. In some embodiments, the antigen is immobilized on a solid support. In some embodiments, the solid support is the surface of a the reaction chamber. In some embodiments, the solid support is of a polymeric membrane (e.g., nitrocellulose strip, Polyvinylidene Difluoride (PVDF) membrane, etc.). Other appropriate solid supports may be used.

In some embodiments, the antibody and antigen binding fragment is immobilized on the solid support prior to contacting with the antigen. In other embodiments, immobilization of the antibody and antigen binding fragment is performed after formation of binding complexes. In still other embodiments, antigen is immobilized on a solid support prior to formation of binding complexes. A detection reagent is added to the reaction chamber to detect immobilized binding complexes. In some embodiments, the detection reagent comprises a detectably labeled secondary antibody directed against the antigen. In some embodiments, the primary antibody or antigen binding fragment is itself detectable labeled, and is thereby the detection reagent.

In one aspect, detection methods comprise the steps of immobilizing antibodies or antigen binding fragments to a solid support; applying a sample (e.g., a biological sample or isolated protein sample) to the solid support under conditions that permit binding of antigen to the antibodies or antigen binding fragment, if present in the sample; removing the excess sample from the solid support; applying detectably labeled antibodies or antigen binding fragments under conditions that permit binding of the detectably labeled antibodies or antigen binding fragments to the antigen-bound immobilized antibodies or antigen binding fragments; washing the solid support and assaying for the presence of label on the solid support.

In some embodiments, the antigen is immobilized on the solid support, such as a PVDF membrane, prior to contacting with the antibody and antigen binding fragment in a reaction chamber (e.g., a membrane bath). A detection reagent is added to the reaction chamber to detect immobilized binding complexes. In some embodiments, the detection reagent comprises a detectably labeled secondary antibody directed against the antigen. In some embodiments, the detection reagent comprises a detectably labeled secondary antibody directed against the primary antibody or antigen binding fragment. As disclosed herein, the detectable label may be, for example, a radioisotope, a fluorophore, a luminescent molecule, an enzyme, a biotin-moiety, an epitope tag, or a dye molecule. In some embodiments, the primary antibody or antigen binding fragment is itself detectable labeled, and is thereby the detection reagent. Suitable detectable labels are described herein, and will be readily apparent to one of ordinary skill in the art.

Accordingly, diagnostic kits, suitable for home or clinical use (point of care service), are provided that comprise (a) detectably labeled and/or non-labeled antibodies or antigen binding fragments, as antigen binding reagents (e.g., sFlt1 isoform binding reagents); (b) a detection reagent; and, optionally, (c) complete instructions for using the reagents to detect antigens in a sample. In some embodiments, the diagnostic kit includes the antibody, or antigen binding fragment, and/or sFlt1 isoform immobilized on a solid support. Any of the solid supports described herein are suitable for incorporation in the diagnostic kits. In a preferred embodiment, the solid support is the surface of a reaction chamber of a plate well. Typically, the plate well is in a multi-well plate having a number of wells selected from: 6, 12, 24, 96, 384, and 1536, but it is not so limited. In other embodiments, the diagnostic kits provide a detectably labeled antibody or antigen binding fragment. Diagnostic kits are not limited to these embodiments and other variations in kit composition will be readily apparent to one of ordinary skill in the art.

EXAMPLES

The following examples are intended to illustrate the disclosure. They are not meant to limit the disclosure in any way.

Example 1: Generation of sFlt and C-Terminal Peptides

Human sFlt1-1 and sFlt1-14 amino acid and protein sequences were determined from GenBank and sequences are provided. Sequences were aligned using VectorNTI (Invitrogen) and unique C-terminal domains were determined by assessing sequence homology (FIG. 1). The sFlt1-1 and sFlt1-14 genes were codon optimized for expression in CHO cells and complete proteins were isolated following expression for 7 days in culture. The sFlt1-14 (14-pep1) and sFlt1-1 (sFlt1-C) peptides were synthesized by New England Peptide and chemically conjugated to KLH through an N-terminal cysteine on each peptide. Additional c-terminal-specific peptides (TRX-Exon14 and GST-1C; FIG. 1) were bacterially expressed and purified for screening ELISAs. All proteins were quantified by measuring optical density at 280 nm in addition to a standard Bradford assay, and purity was analyzed by Coomassie stained SDS-PAGE.

Example 2: Generation of Total sFlt1 and Isoform-Specific Monoclonal Antibodies

CD-1 wild type mice or HuMAb mice were immunized with full-length sFlt1, sFlt1-C, 14-pep1 or 1C-KLH-18. The antigen was administered in combination with the Sigma adjuvant system and mouse sera responses and subsequent hybridoma cultures following splenic fusion were monitored by enzyme linked immunosorbent assay (ELISA) to the full-length sFlt1-1 and sFlt1-14 (FIG. 1B) or isoform-specific peptides GST-1C and TRX-Exon14 (FIG. 1). Mice that were determined to have a strong immune response to the relevant antigen were selected for splenic B cell isolation, which were fused to mouse myeloma cells using standard spleen cell fusion methods. Clonal hybridomas were generated and screened using ELISA for production of mAbs reactive to total sFlt, sFlt1-1 or sFlt1-14. This method yielded 359 positive murine clones. Of the 359 total positive murine clones, several had specific activity only to sFlt1-1 (FIG. 2A) or sFlt1-14 (FIG. 2B) as shown by ELISA. Mouse mAb 10 ugR#9 was selected for its ability to bind both full length sFlt1-1 and sFlt1-14 (FIGS. 4A and 4B), but not the isoform-specific peptides GST-1C or TRX-Exon14 (FIG. 2). Of the isoform-specific clones shown in FIG. 2, mouse mAb 1CKLH18 and Ex14-1 were selected for their specific binding properties to sFlt1-1 and sFlt1-14, respectively (FIGS. 4A and 4B).

Example 3: Antibody Characterization

Antibody Heavy Chain Sequence Determination

RNA was extracted from the positive hybridoma clones and nucleotide sequences of the heavy chain of the reactive antibody determined. RNA was purified from all hybridomas and RT-PCR performed using a reverse oligonucleotide complimentary to the heavy chain constant region and a forward oligonucleotide cocktail designed to anneal to all heavy chain genes expressed in the mouse. PCR products were sequenced and those with unique CDR regions were scaled forward (the sequences for antibodies selected for final ELISA assays are included).

ELISA

To determine reactivity of unique antibodies with sFlt1-1 and sFlt1-14, ELISA was employed. As described above, TRX-Exon14 and GST-1C peptides were expressed and purified from bacteria. ELISA plates were coated with either GST-1C (FIG. 2A) or TRX-Exon14 (FIG. 2B), blocked with BSA and a series of dilutions of each hybridoma supernatant containing mAb was incubated on the coated plates. Bound antibody was detected with anti-mouse alkaline phosphatase secondary antibody and the interaction developed with PNPP. Plates were read using a Molecular Devices Emax plate reader and antibodies with the desired specificity and highest affinity were selected for final ELISA production. These included mouse mAbs EX14-1 to detect sFlt1-14 and 1C-KLH-18 to detect sFlt1. The mouse total sFlt mAb (10 ugR#9) was developed using similar methods and screening by ELISA with full-length human recombinant sFlt1-1 and sFlt1-14 expressed and purified from CHO cells. A human anti sFLT antibody with properties described above (under Quantitative Capture ELISA) was also used to minimize background in the ELISAs.

Western Blots

Specificity of mAbs to sFlt1-14 and SFlt1-1 was investigated by western blot analysis on human amniotic fluid (FIG. 3). Briefly, human amniotic fluid was concentrated in a 10 MWCO iCON protein concentrator (Pierce) and 15 µl was mixed 1:1 with reducing sample buffer and loaded onto 12% polyacrylamide gels. As standards, human recombinant sFlt1-1 or sFlt1-14 was loaded in final quantities of 200, 100 and 50 ng. After electrophoresis and transfer to nitrocellulose membranes, blots were blocked in 5% BSA and probed with EX14-1 (FIG. 3A), 1C-KLH-18 (FIG. 3B) or a commercially available mouse anti-VEGFR1 mAb (FIG. 3C) that recognized a single protein in amniotic fluid at the expected molecular weight (~115 kDa) that corresponds to recombinant human sFlt1-14 and sFlt1-1, respectively. After washing, an HRP-labeled anti-mouse secondary antibody was used to detect bound mAb, developed and visualized using a Kodak Gel Logic imaging system. In addition, both mouse mAbs specifically recognized their recombinant sFlt1 isoform standards by western blot. These data confirm the ELISA results suggesting the mouse antibodies were specific for their sFlt1 isoforms and recognized their endogenous sFlt1 isoform in biological fluid.

Affinity

The $K_D$ of mAb EX14-1 and 1CKLH18 was measured to be $3.95 \times 10^{-8}$ M and $4.30 \times 10^{-9}$ M, respectively, by Octet analysis. In comparison, the $K_D$ of mAb 10 ugR#9 was $5.4 \times 10^{-9}$ M and the human mAb used as a capture antibody was $2.57 \times 10^{-9}$ M. The nanomolar or near-nanomolar affinities of these mAbs make them sensitive reagents for a diagnostic assay with quantitative capabilities.

Example 4: Quantitative Capture ELISA of sFlt1-1 and sFlt1-14 and Specificity of mAbs To measure the concentration of total sFlt and its isoforms, sFlt1-1 and sFlt1-14, in biological fluid, a capture ELISA was developed. Using an anti-sFlt human antibody to capture total sFlt and mouse antibodies 10 ugR#9, EX14-1 or 1C-KLH-18 to detect bound sFlt, allows the efficient capture of sFlt in biological fluid without high background or interference (FIG. 4). The total sFlt-specific mAb, 10 ugR#9, detects both recombinant human sFlt1-1 (FIG. 4A) and sFlt1-14 (FIG. 4B) expressed and purified from CHO cells at comparable sensitivities. The sFlt1-specific mAb, 1C-KLH-18, detects recombinant human sFlt1-1, but not sFlt1-14 (FIG. 4A,B). Conversely, the sFlt1-14-specific mAb, EX14-1, detects recombinant human sFlt1-14, but not sFlt1-1 (FIG. 4A,B). In addition, each mAb detects a protein in human amniotic fluid (known from the literature to contain both sFlt isoforms; FIG. 4C) and no background is observed in normal human sera, which should contain very low levels of sFlt isoforms (FIG. 4D).

Using human recombinant sFlt1-14 to generate standard curves, sFlt1-14 concentration in amniotic fluid was quantified (FIG. 4E). As expected, protein was not detected in normal human sera (<0.02 ng/ml) and when 25 ng/ml of human recombinant sFlt1-14 was added to the sera sample, both mAbs 10 ugR#9 and EX14-1 quantified the spiked sFlt1-14 appropriately (27.32 and 27.77 ng/ml, respectively; FIG. 4E). These results indicate the mAbs are specific for sFlt and do not recognize additional proteins in biological fluid, while also avoiding any interference with specific protein detection that could be caused by biological fluid. Quantification of sFlt in amniotic fluid indicated levels of total sFlt at 21.87 ng/ml and sFlt1-14 at 16.64 ng/ml (FIG. 4E). Similar to sera samples, 25 ng/ml of sFlt1-14 added to amniotic fluid quantified appropriately, as the total levels detected approximately equaled the sum of spiked sFlt1-14 plus the endogenous sFlt levels measured (47.4 ng/ml for 10 ugR#9 and 36.63 ng/ml for EX14-1; FIG. 4E). These results show the mAbs in the present disclosure are able to specifically recognize sFlt in human biological samples without interference in quantitation. To further ensure mAbs are specific for sFlt1-1 and sFlt1-14 in biological fluid, western blots were performed on human amniotic fluid (FIG. 3). Both EX14-1 (FIG. 3A) and 1C-KLH-18 (FIG. 3B) recognize a single protein in amniotic fluid at the expected molecular weight (~80 kDa) that corresponds to recombinant human sFlt1-14 or sFlt1-1 standards. Also included as a positive control is a commercially available mAb (Sigma Cat.#V4262) that recognizes total sFlt (FIG. 3C).

Example 5: Detection of sFlt1-1 and sFlt1-14 in Human Pregnant Sera Using Capture ELISA The capture ELISA format as described above was used to detect total sFlt, sFlt1-14 and sFlt1-1 in sera from pregnant women. Literature reports indicate that in most pregnancies sFlt levels rise during late stages, even in healthy pregnancies. Accordingly, six serum samples from women during their third trimester (weeks 36-39 of gestation) were analyzed and determined to have increased levels of total sFlt, sFlt1-14 and sFlt1-1 as compared to non-pregnant control samples (FIG. 5). Interestingly, levels of sFlt1-14 were equal to or higher than sFlt1-1, suggesting the sFlt1-14 isoform may be the major contributor to total circulating sFlt levels in pregnant women.

Longitudinal serum samples were prospectively collected under IRB approval from pregnant women and analyzed for their concentration of sFlt1 splice variants using a capture ELISA format with mAbs Ex14-1 and 1CKLH18 to detect sFlt1-14 and sFlt1-1 splice variants, respectively. These results were compared to the concentration of total sFlt1 levels (VEGFR-1) that had been measured previously for each sample using a Quantikine ELISA Kit. The concentrations of serum sFlt1-1, sFlt1-14 and total sFlt1 (VEGFR-1) were compared between women with a singleton gestation who developed preeclampsia (PE) to those women who did not develop preeclampsia (Control) (FIG. 10A-10C) for three gestational age windows (GW): 21-27.99 weeks (GW1); 28-31.99 weeks (GW2): and >32 weeks (GW3). Concentrations of the sFlt1-1 variant were significantly higher in women with preeclampsia (N=13) compared to controls (N=124) for the earliest gestational window (GW1). In addition, sFlt1-1 and sFlt1-14 measurements were both significantly higher in women with preeclampsia (N=12) compared to controls (N=115) in GW2. VEGFR-1 measurements were not significantly different between women with preeclampsia as compared to controls for GW1 and GW2; however, VEGFR-1, sFlt1-1 and sFlt1-14 concentrations were significantly different between women with preeclampsia (N=10) compared to control women (N=121) for GW3.

Example 6: Prediction of Preeclampsia in Pregnant Women

Using the capture ELISA format as described above with mAbs EX14-1 and 1C-KLH-18 to detect sFlt splice variants in serum, preeclampsia can be predicted in pregnant women meaningfully prior to onset. Serum samples are analyzed as described above and compared to human recombinant sFlt1-1 and sFlt1-14 standards to determine absolute circulating quantities. The absolute measurement of circulating sFlt1-14 and/or sFlt1-1, or the ratio of sFlt1-14 to sFlt1-1, is compared to a reference standard comprised of a group of known healthy pregnancies matched for week of gestation at the time of sampling and other basic parameters including: BMI, nulliparous, singleton/multiple gestation, previous preeclampsia, hypertension, diabetes and renal disease.

A logistic regression analysis for all women included in the study was performed to examine if any of the risk factors were independently associated with the development of preeclampsia. The presence of pre-existing chronic hypertension and/or diabetes mellitus was associated with an increased risk of developing preeclampsia (Wald chi-square=6.26, 1 d.f., p=0.0123). Therefore, comparisons of VEGFR-1 and both splice variants were performed for the subset of women with pre-existing chronic hypertension and/or diabetes mellitus who developed preeclampsia (chtn_dm PE; N=9) or not (chtn_dm Controls; N=29) (FIG. 10D-10F). For GW2 and GW3, VEGFR-1, sFlt1-1 and sFlt1-14 were significantly higher in those women who developed preeclampsia compared to controls with similar co-morbidities. Statistical differences for sFlt1-1 and sFlt1-14 were greater at GW2 when compared to VEGFR-1.

Figure 11A:
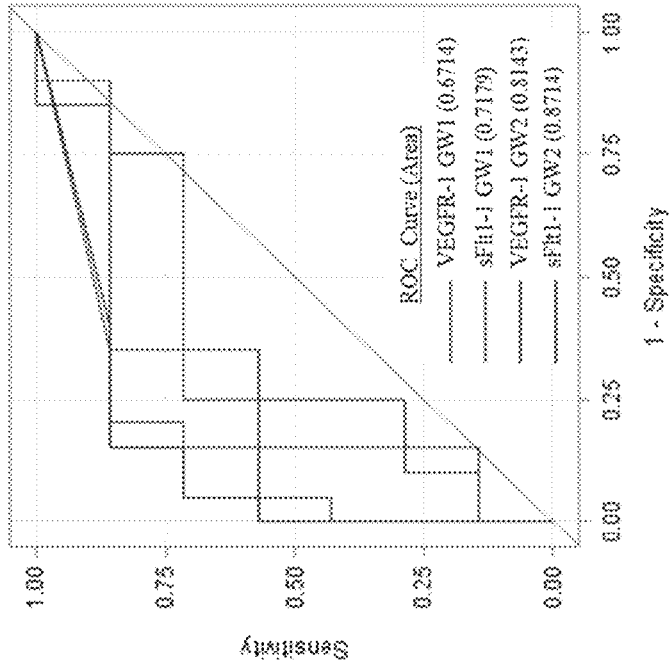
FIGS. 11A-11B show receiver operator curves generated from the sensitivity and specificity of sFlt1-1 and VEGFR-1 preeclampsia predictions at gestational windows 1 and 2 in (FIG. 11A) all samples measured and (FIG. 11B) a high risk subset of these women with chronic hypertension and/or diabetes mellitus.
Figure 11B:
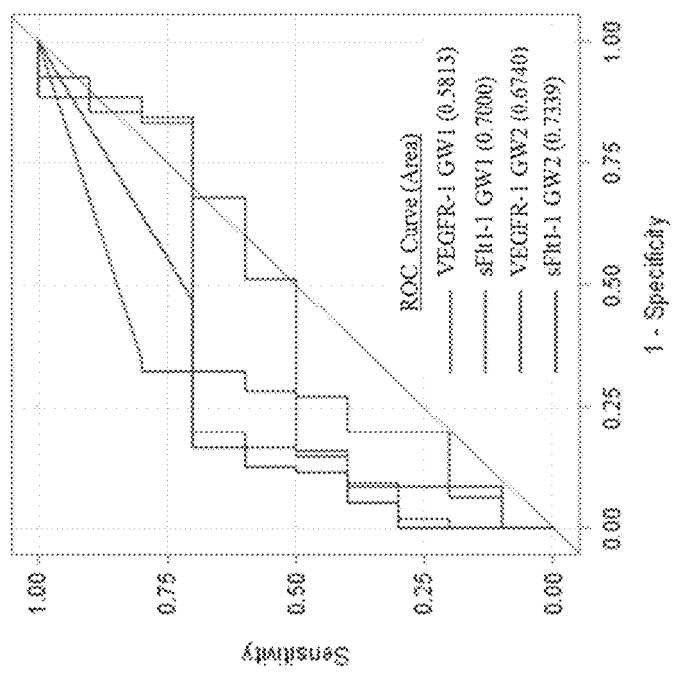

These results suggest measurement of sFlt1 isoforms, particularly sFlt1-1, may be more predictive of preeclampsia as compared to VEGFR-1 (total sFlt1). Thus, receiver operator curves (ROC) were generated for subjects who had samples at both GW1 and GW2 time points (FIG. 11). The area under the curve (AUC) for sFlt1-1 was greater as compared to VEGFR-1 for both GW1 and GW2 (FIG. 11A) and furthermore the sFlt1-1 AUC at GW1 was comparable to that of VEGFR-1 at GW2. For subjects who developed preeclampsia, the GW1 sample was collected, on average, 10.2 weeks before preeclampsia diagnosis while collection at GW2 was a mean of 6.99 weeks prior to diagnosis, suggesting that sFlt1-1 may be as predictive as VEGFR-1 at least three weeks earlier. Similarly, the AUC is greater for sFlt1-1 compared to VEGFR-1 at both gestational windows for the subset of women with chronic hypertension and/or diabetes mellitus (FIG. 11B).

SUMMARY

Development of the sFlt1 isoform-specific mAbs was accomplished using the carboxy-terminus peptides described in conjunction with standard immunization and hybridoma techniques. These antibodies had high affinities and could specifically recognize their appropriate isoforms from both recombinant and endogenous sources. Using the mAbs in a capture ELISA format yielded an assay with high sensitivity to quantitate the sFlt1 isoforms in human serum.

The ability of these mAbs to measure sFlt1-1 and sFlt1-14 isoforms was assessed in human serum samples prospectively collected from pregnant women and compared these results to total sFlt1 (VEGFR-1) measured using a commercial kit similar or identical to what has been used in previous studies that include sFlt1 as a predictive biomarker for preeclampsia. Of note, the sFlt1-14 epitope used to generate the sFlt1-14-specific mAb is shared with two other sFlt1 isoforms, sFlt1_v3 and sFlt1_v4; however, these isoforms have been shown to represent a very small portion of total sFlt1 (<1% of total sFlt1 mRNA transcripts).

Measurement of sFlt1 isoforms collected prospectively from pregnant women surprisingly indicated sFlt1-1 is the predominant isoform in the maternal circulation, as opposed to sFlt1-14, even in women who later developed preeclampsia. Results provided herein show that statistically significant difference in mean sFlt1 concentrations at the earliest gestational window between those women who developed preeclampsia compared to those who did not suggests the sFlt1-1 isoform may be a more predictive biomarker than total sFlt1 (also referred to herein as VEGFR-1). This conclusion was further supported by the greater area under the receiver operator curves and could be applied to a high risk cohort of pregnant women with hypertension and/or diabetes mellitus who were part of the study. Improved predictability of sFlt1-1 isoform as a biomarker (as compared to total sFlt1) is associated with antibody specificity. The total sFlt1 assay not only measures all isoforms of sFlt1, including sFlt1-1 and sFlt1-14, but also recognizes VEGFR-1 surface receptor proteolytically cleaved from cell membranes, which can be introduced into the circulation. Evidence suggests this mechanism is a possible significant source of soluble VEGFR-1 and if background levels of membrane-cleaved soluble VEGFR-1 are similar among women with and without preeclampsia, this may confound the actual biomarker differences attributed to preeclampsia using prior techniques that focus on total sFlt1.

Isoform-specific ELISAs disclosed herein were performed using a 4-fold initial dilution of serum, with the lower limit of quantitation at 1.2 ng/ml. As a result, a significant number of samples were below the lower limit of quantitation, particularly in the sFlt1-14 assay. In some embodiments, it is desirable to achieve sensitivity of the ELISA such that sFlt1 isoform levels are quantifiable close to the lower limit of detection (300 pg/ml in the present study). In some embodiments, total sFlt1 detector mouse mAb, 10 ugR#9, permits bridging of the sFlt1-1 and sFlt1-14 ELISAs and indicates absolute quantitation of sFlt1-1 and sFlt1-14 can be directly compared within a sample.

Furthermore, excellent spike recovery was shown at 25 ng/mL and low background (<0.02 ng/mL) was demonstrated in the developmental assays using relevant sample matrix as described in Example 4. Thus, assays for sFlt1-1 and sFlt1-14 may be performed using antibodies of the present disclosure and having lower limits of quantitation and lower limits of detection at or below nanogram levels providing the highly sensitive and specific tools.

In summary, mouse monoclonal antibodies that bind to sFlt1 variants sFlt1-1 and sFlt1-14 have been developed. In human sera, these mAbs were able to detect statistically significant differences in concentrations of sFlt1 isoforms between women who develop preeclampsia and those who do not. These isoform-specific biomarkers may more accurately predict preeclampsia in both low risk and a high risk group of pregnant women with pre-existing hypertension and diabetes mellitus, which could impact the management of their medical care.

Materials and Methods

Throughout the examples, the following materials and methods were used unless otherwise stated. In general, the practice of the present disclosure employs, unless otherwise indicated, conventional techniques of chemistry, molecular biology, recombinant DNA technology, immunology (especially, e.g. antibody technology), and standard techniques in polypeptide preparation. See, e.g., Sambrook, Fritsch and Maniatis, *Molecular Cloning: Cold Spring harbor Laboratory Press* (1989); *Antibody Engineering Protocols (Methods in Molecular Biology)*, 510, Paul, S., Humana Pr (1996); *Antibody Engineering: A Practical Approach* (Practical Approach Series, 169), McCafferty, Ed., Irl Pr (1996); *Antibodies: A Laboratory Manual*, Harlow et al., C.S.H.L. Press, Pub. (1999); and *Current Protocols in Molecular Biology*, eds. Ausubel et al., John Wiley and Sons (1992)

sFlt and C-Terminal Peptide Generation
CHO Cell Expression and Purification of Full-Length sFlt Isoforms Human sFlt1-1 and sFlt1-14 amino acid and protein sequences were determined from GenBank (AAC50060.1 and EU368830.1, respectively) and a codon-optimized gene encoding the sFlt1-1 (SEQ ID NO. 35; FIG. 1) or sFlt1-14 protein (SEQ ID NO. 37; FIG. 1) was synthesized by Integrated DNA Technologies (IDT) and the sequence confirmed. The gene was subcloned from the vector provided from IDT into pcDNA3.1 (Life Technologies) in frame with a C-terminal 6-histidine tag. To express sFlt, CHO cells were transiently transfected with the vector containing the gene. Briefly, cells at a density of 1×10^6 were seeded in CD-CHO media (Life Technologies)+6 mM L-glutamine 24 hours before transfection of pcDNA3.1 vector at 1 ug/ml of culture diluted in Opti-MEM (Life Technologies). Prior to transfection, linear 25 kDa polyethylenimine (PEI; Sigma) was added to DNA (1:5 ratio of DNA/PEI) and incubated at room temperature for 15 minutes. Cells were resuspended in fresh media and the transfection mix was added drop-wise to each flask while swirling. Cells were maintained at 37° C. and 5% $CO_2$ with shaking for seven days before culture supernatant was harvested for protein isolation. Approximately 30 mL of Heparin Sepharose 50/50 bead slurry (Biorad) was added to 1 L of culture supernatant and mixed for 3 hours at room temperature with shaking. Beads were loaded onto protein purification columns (Biorad) and washed three times with PBS. sFlt was eluted with PBS+1M sodium chloride, which was subsequently dialyzed in PBS overnight using a 10 k MWCO Slide-A-Lyzer (Pierce). Purified sFlt1-1 and sFlt1-14 samples were quantified by absorbance at 280 nm and a standard Bradford assay. Purity and concentration were analyzed by Coomassie stained SDS-PAGE analysis, western blot and ELISA using anti-VEFGR1 antibody (AF321; R&D Systems).

Bacterial Expression of sFlt1-1 and sFlt1-14 C-Terminal Peptides

Isoform protein sequences were aligned using VectorNTI (Invitrogen) and unique C-terminal domains were determined by assessing sequence homology. The isoform-specific peptides, 14-pep1 (sFlt1-14) and sFlt1-C (sFlt1-1), were synthesized and chemically conjugated to keyhole limpet hemocyanin (KLH) through an N-terminal cysteine on each peptide (FIG. 1). In addition, bacterially codon-optimized genes encoding c-terminal peptides from sFlt1-1 and sFlt1-14 (FIG. 1) were synthesized by IDT and the sequence confirmed. The gene was subcloned from the vector provided from IDT into pET32a(+) (EMD) in frame with an upstream thioredoxin (TRX) with 6-histidine tag or glutathione 5-transferase (GST) fusion protein using BamHI and SalI. BL21Star BL21Star *Escherichia coli* cells (Invitrogen) were transformed with the vector containing the gene and grown overnight at 37° C. in Luria-Bertani broth containing 100 μg/ml ampicillin (LB-amp). The culture was diluted 1:10 in LB-amp and grown for 2.5 hours at 37° C. followed by addition of 1 mM isopropyl-β-D-thiogalactopyranoside and further grown at 37° C. for 2.5 hrs. Bacteria were harvested by centrifugation and pellets were frozen at −20° C. Protein was isolated using standard Ni-NTA agarose or Glutathione sepharose bead purification and dialyzed in PBS. Protein was quantified by absorbance at 280 nm and purity was analyzed by SDS-PAGE.

Antibody Production
Mouse Immunizations

To generate mouse mAbs specific for total sFlt, sFlt1-1 and sFlt1-14, wild type CD-1 mice (Jackson Laboratories) or HuMAb mice were injected intraperitoneally weekly for up to 14 weeks with 10-50 ug of sFlt1, 14-pep1 (SEQ ID NO.42) or sFlt1-C (SEQ ID NO. 43) mixed with the Sigma adjuvant system (Sigma) per the manufacturer's protocol. Mouse sera responses were monitored by ELISA to determine the appropriate time for splenic fusion, which was generally indicated by a detectable titer against the immunizing protein at >4000-fold dilution of serum.

Splenic Fusions and Hybridoma Selection

Mouse spleens were harvested and spleen cells were isolated and fused to mouse myeloma cells (P3X-AG8.653) following a standard PEG fusion protocol to generate hybridomas. Hybridoma supernatants were screened for production of antibody reactive to sFlt1-1, sFlt1-14, TRX-Exon14 (SEQ ID NO. 40) and GST-1C (SEQ ID NO. 38) by ELISA, Positive clonal hybridoma cell cultures were expanded for further characterization and production of mAbs. Isolation of mAbs from culture supernatant was performed using standard Protein A purification techniques.

ELISA

To determine reactivity of unique antibodies with sFlt1-1. sFlt1-14, TRX-Exon14 (SEQ ID NO. 40) and GST-1C (SEQ ID NO. 38) isoforms, ELISA plates were coated with either GST-1C or TRX-Exon14, blocked with BSA and a series of dilutions of each hybridoma supernatant containing mAb (or purified mAb) was incubated on the coated plates. Bound antibody was detected with anti-mouse alkaline phosphatase secondary antibody (Jackson ImmunoResearch) and the interaction developed with pNPP. Plates were read using a Molecular Devices Emax plate reader at 405 nm and antibodies with the desired specificity and highest apparent affinity were selected. Total sFlt1-specific mAbs were developed using similar methods except screening by ELISA utilized full-length human recombinant sFlt1-1 and sFlt1-14 expressed and purified from CHO cells in place of isoform-specific peptides.

Isolation and Sequencing of Hybridoma Antibody Genes

RNA was isolated from hybridoma cells using a Qiagen RNeasy kit as described by the manufacturer. RT-PCR was performed for the heavy chain variable region with gene-specific primers containing restriction sites, the resulting sequence was cloned and the construct was sequenced. Rapid Amplification of mRNA Ends by PCR (RACE) was performed for the light chain variable region with gene-specific primers. The sequence was cloned into the pCR4-TOPO vector (Invitrogen) and the inserted element was sequenced. Gene specific primers were designed and used to PCR-amplify sequences from pCR4-TOPO and add restriction sites for subsequent cloning into expression vectors.

Antibody Affinity

Affinity of antibodies was determined using an Octet QK (ForteBio) biomolecular interaction instrument. The Octet QK performs similarly to Biacore in the measurement of antibody affinity. The Octet QK uses biosensors to assess mass increases/decreases and determine rates of association and disassociation. Anti-murine or anti-human biosensors (ForteBio) were used to capture mAb in PBS (5 ug/ml) to saturation and unbound mAb was washed away. The coated biosensors were introduced into a solution containing recombinant human sFlt1-1 or sFlt1-14 at which time $K_{on}$ was determined. The sensor was then introduced into a buffer solution and the $K_{off}$ determined. Using $K_{on}$ and $K_{off}$ an affinity ($K_D$) was calculated. Reference wells were included that did not contain mAb during the capture step as well as control wells that contained either irrelevant mAb during the capture step or irrelevant antigen during the binding step. All references and controls displayed negligible binding.

Western Blots

Briefly, human amniotic fluid (collected under an approved IRB protocol) was concentrated in a 10 MWCO iCON protein concentrator (Pierce) and 15 µl was mixed 1:1 with reducing sample buffer and loaded onto 12% polyacrylamide gels. As standards, human recombinant sFlt1-1 or sFlt1-14 was loaded in final quantities of 200, 100, 50 or 25 ng. After electrophoresis and transfer to nitrocellulose membranes, blots were blocked in 5% BSA and probed with Ex14-1, 1CKLH18 or a commercially available mouse anti-VEGFR1 mAb that recognizes a shared epitope with total sFlt1 (Sigma Cat.#V4262). After washing, an HRP-labeled anti-mouse secondary antibody (Jackson ImmunoResearch) was used to detect bound mAb, developed with ECL Prime detection reagent (GE Healthcare) and visualized using a Kodak Gel Logic imaging system.

Quantitative Capture ELISA

A capture ELISA format was utilized to quantify the total sFlt, sFlt1-1 or sFlt1-14 concentration in solution. Briefly, high-binding ELISA plates (Costar) were coated with 1 ug/ml of an anti-sFlt human antibody overnight at 4° C. This anti-sFlt antibody was selected to provide a capture reagent that bound both sFlt1-1 and sFlt1-14 at an epitope in their homologous regions without interfering with the availability of the epitopes bound by the antibodies of the present disclosure. Plates were washed in PBS+0.1% Tween-20 and blocked in 5% BSA/PBS+0.1% Tween-20 for one hour. Recombinant sFlt1-1 or sFlt1-14 (used as reference standards) diluted in PBS, normal human sera (SunnyLabs) or amniotic fluid (collected under an approved IRB protocol), or a 1:2 starting dilution of human sera or amniotic fluid in PBS was serially diluted (1:2) onto ELISA plates and incubated for 1 hour at room temperature on a plate shaker at 550 rpm. After washing, one of three mouse primary antibodies were added: 10 ugR#9 (detects total sFlt), EX14-1 (detects sFlt1-14) or 1C-KLH-18 (detects sFlt1) and incubated for one hour at room temperature. Excess primary antibody was washed and either AP or HRP conjugated anti-mouse IgG (Jackson ImmunoResearch) was incubated in wells for 45 minutes at room temperature. Following extensive washing, p-nitrophenyl phosphate disodium salt (PNPP) at 1 mg/ml (for AP conjugates) or 1-step Ultra TMB ELISA detector reagent (Pierce; for HRP conjugates) was used according to manufacturer's instructions and absorbance at 405 nm (for pNPP) or 450 nm (for Ultra TMB) was analyzed using a Molecular Devices Emax plate reader with Softmax Pro 5.4.4 software.

For prospectively collected subject samples, the lower limit of detection for sFlt1-1 and sFlt1-14 was determined to be 300 pg/ml by analysis of standard curves. Thus the lower limit of quantitation was set at 1.2 ng/ml given the 4-fold initial serum dilution. For statistical analyses, samples below the lower limit of quantitation were assigned a value equal to one-half the lower limit of quantitation, e.g. 0.6 ng/ml.

Total sFlt1 (VEGFR-1) measurement in prospectively collected subject samples were performed. Briefly, the Human sVEGFR1/Flt-1 Quantikine ELISA Kit (R&D Systems) was used. Samples at a 10 or 20 fold dilution were measured in duplicate and absolute quantities were quantified based off the recombinant standard protein included in the kit.

Subjects and Serum Samples for Measurement of sFlt1 Isoforms

The laboratory analysis of sFlt1 isoforms as predictive biomarkers for the development of preeclampsia was performed. Serum samples used in this analysis were obtained prospectively from pregnant women. Briefly, samples were collected at approximately three time points: 1) 21-27 weeks gestation; 2) 28-31 weeks gestation; and 3) 32-35+ weeks gestation. All samples were stored frozen until use. Subject information collected as part of the protocol included: a) Risk cohort (low or high); b) Maternal outcome, c) Singleton or multiple gestation; d) Gestational age at each blood draw; e) Gestational age at time of preeclampsia diagnosis, if applicable; and f) Gestational age at delivery. Women were considered at high risk for preeclampsia if they had at least one of the following factors during pregnancy: chronic hypertension; pre-gestational diabetes mellitus; obesity, preeclampsia history and/or multiple gestations. Maternal outcome was assessed at delivery and included the following choices: 1) no pregnancy induced hypertension, 2) gestational hypertension, 3) early preeclampsia (<34 weeks gestation), 4) late preeclampsia (≥34 weeks gestation) and 4) preeclampsia severity (mild vs severe).

Statistics

Comparisons of sFlt1 proteins were performed between those women who eventually developed preeclampsia and those who did not develop preeclampsia at each gestational window. Changes in levels of sFlt1-1, sFlt1-14 and VEGFR-1 (total sFlt1) over time were expressed as means±standard error. The means within each gestational window were compared using a standard t-test with unequal variances. Receiver operator curves (ROC) were generated from logistic models with diagnosed preeclampsia (yes/no) as the binary outcome and, as predictors, VEGFR-1 and sFlt1-1 values in gestational window 1 (21-27 weeks) and gestational window 2 (28-31 weeks). ROCs were generated for all women and for a subset of these women with pre-existing chronic hypertension and/or diabetes. Areas under the curves (AUC) were calculated using the trapezoidal method. Although the prospective study had pre-defined weeks for each of the three gestational windows, two samples for a single woman may have been collected within the same window due to scheduling logistics, which occurred in 13 instances out of 480 total measurements (2.7%). In these cases, one of the two measurements in the window was moved to the next closest window to avoid multiple measurements within one window from the same subject. In each instance, the sample moved to another gestational window was collected less than one week outside the pre-defined gestational window parameters. Women who were diagnosed with preeclampsia prior to sample collection were not included in the predictive modeling for that, or subsequent, window(s). Multiple gestation pregnancies were excluded for these analyses, as biomarker profiles are significantly different in the presence or absence of preeclampsia compared to singletons. All analyses were performed using SAS 9.3 (SAS Institute, Inc., Cary, N.C.).

Other Embodiments

The description of the specific embodiments of the disclosure is presented for the purposes of illustration. It is not intended to be exhaustive or to limit the scope of the disclosure to the specific forms described herein. Although the disclosure includes reference to several embodiments, it will be understood by one of ordinary skill in the art that various modifications can be made without departing from the spirit and the scope of the disclosure.

All patents, patent applications, and publications referenced herein are hereby incorporated by reference. Other embodiments are in the claims.

What is claimed is:

1. A monoclonal antibody, or antigen binding fragment thereof, that specifically binds to soluble FMS-like tyrosine kinase (sFlt1) protein and that comprises six complementarity determining regions (CDRs): CDRH1, CDRH2, CDRH3, CDRL1, CDRL2, and CDRL3, wherein CDRH1 comprises the sequence of SEQ ID NO: 3, CDRH2 comprises the sequence of SEQ ID NO: 5, CDRH3 comprises the sequence of SEQ ID NO: 7, CDRL1 comprises the sequence of SEQ ID NO: 11, CDRL2 comprises the sequence of SEQ ID NO: 13, and CDRL3 comprises the sequence of SEQ ID NO: 15; or wherein CDRH1 comprises the sequence of SEQ ID NO: 19, CDRH2 comprises the sequence of SEQ ID NO: 21, CDRH3 comprises the sequence of SEQ ID NO: 23, CDRL1 comprises the sequence of SEQ ID NO: 27, CDRL2 comprises the sequence of SEQ ID NO: 29, and CDRL3 comprises the sequence of SEQ ID NO: 31.

2. The monoclonal antibody, or antigen binding fragment thereof, of claim 1, wherein CDRH1 comprises the sequence of SEQ ID NO: 3, CDRH2 comprises the sequence of SEQ ID NO: 5, CDRH3 comprises the sequence of SEQ ID NO: 7, CDRL1 comprises the sequence of SEQ ID NO: 11, CDRL2 comprises the sequence of SEQ ID NO: 13, and CDRL3 comprises the sequence of SEQ ID NO: 15, and wherein the monoclonal antibody binds specifically to sFlt1 variant 1 (sFlt1-1).

3. The monoclonal antibody, or antigen binding fragment thereof, of claim 2, comprising the heavy chain variable domain sequence of SEQ ID NO: 1.

4. The monoclonal antibody, or antigen binding fragment thereof, of claim 2, comprising the light chain variable domain sequence of SEQ ID NO: 9.

5. The monoclonal antibody, or antigen binding fragment thereof, of claim 2, comprising the heavy chain variable domain sequence of SEQ ID NO: 1 and the light chain variable domain sequence of SEQ ID NO: 9.

6. The monoclonal antibody, or antigen binding fragment thereof, of claim 1, wherein CDRH1 comprises the sequence of SEQ ID NO: 19, CDRH2 comprises the sequence of SEQ ID NO: 21, CDRH3 comprises the sequence of SEQ ID NO: 23, CDRL1 comprises the sequence of SEQ ID NO: 27, CDRL2 comprises the sequence of SEQ ID NO: 29, and CDRL3 comprises the sequence of SEQ ID NO: 31, and wherein the monoclonal antibody binds specifically to sFlt1 variant 14 (sFlt1-14).

7. The monoclonal antibody, or antigen binding fragment thereof, of claim 6, comprising the heavy chain variable domain sequence of SEQ ID NO: 17.

8. The monoclonal antibody, or antigen binding fragment thereof, of claim 6, comprising the light chain variable domain sequence of SEQ ID NO: 25.

9. The monoclonal antibody, or antigen binding fragment thereof, of claim 6, comprising the heavy chain variable domain sequence of SEQ ID NO: 17 and the light chain variable domain sequence of SEQ ID NO: 25.

10. The monoclonal antibody, or antigen binding fragment thereof, of claim 1, wherein the monoclonal antibody, or antigen binding fragment, is a humanized antibody, a diabody, a chimeric antibody, a Fab fragment, a F(ab')2 fragment, or an Fv fragment.

11. The monoclonal antibody, or antigen binding fragment thereof, of claim 1, wherein the monoclonal antibody, or antigen binding fragment, comprises a heavy chain constant domain selected from the group consisting of IgG, $IgG_1$, $IgG_2$, $IgG_{2A}$, $IgG_{2B}$, $IgG_{2C}$, $IgG_3$, $IgG_4$, $IgA_1$, $IgA_2$, IgD, IgM, and IgE constant domains.

12. The monoclonal antibody, or antigen binding fragment thereof, of claim 1, wherein the monoclonal antibody, or antigen binding fragment, is conjugated to an agent selected from the group consisting of a fluorescent agent, a luminescent agent, an enzymatic agent and a radioactive agent.

* * * * *

UNITED STATES PATENT AND TRADEMARK OFFICE
CERTIFICATE OF CORRECTION

PATENT NO. : 10,421,812 B2
APPLICATION NO. : 15/086445
DATED : September 24, 2019
INVENTOR(S) : Teresa Broering et al.

Page 1 of 1

It is certified that error appears in the above-identified patent and that said Letters Patent is hereby corrected as shown below:

In the Specification

At Column 1, Line 17, reading:
"UL1TR000161"

Should read:
--TR000161--

Signed and Sealed this
Twenty-sixth Day of May, 2020

Andrei Iancu
*Director of the United States Patent and Trademark Office*

SEQUENCE LISTING

```
<160> NUMBER OF SEQ ID NOS: 45

<210> SEQ ID NO 1
<211> LENGTH: 118
<212> TYPE: PRT
<213> ORGANISM: Artificial Sequence
<220> FEATURE:
<223> OTHER INFORMATION: Synthetic Polypeptide

<400> SEQUENCE: 1

Glu Val Gln Leu Gln Gln Ser Gly Ala Glu Leu Val Arg Pro Gly Ala
1               5                   10                  15

Ser Val Lys Leu Ser Cys Thr Ala Ser Gly Val Asn Ile Lys Asp Asp
            20                  25                  30

Tyr Met Asn Trp Val Asn Gln Arg Pro Glu Gln Gly Leu Glu Trp Ile
        35                  40                  45

Gly Trp Ile Asp Pro Glu Asn Gly Asp Thr Glu Tyr Ala Ser Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Ala Gly Tyr Asp Tyr Phe Pro Phe Val Tyr Trp Gly Gln Gly Thr
            100                 105                 110

Leu Val Ala Val Ser Ala
        115

<210> SEQ ID NO 2
<211> LENGTH: 354
<212> TYPE: DNA
<213> ORGANISM: Artificial Sequence
<220> FEATURE:
<223> OTHER INFORMATION: Synthetic Polynucleotide

<400> SEQUENCE: 2
gaggttcagc tgcagcagtc tggggctgag cttgtgaggc cagggggcctc agtcaagttg      60 tcctgcacag cttctggcgt taatattaaa gacgactata tgaattgggt gaatcagagg     120
cctgaacagg gcctggagtg gattggatgg attgatcctg agaatggtga tactgaatat     180
```

```
gcctcgaagt tccagggcaa ggccactata acagcagaca catcctccaa cacagcctac      240
ctgcagctca gcagcctgac atctgaggac actgccgtct attactgtgc tgcaggttat      300
gattacttcc cctttgttta ctggggccaa gggactctgg tcgctgtctc tgca            354
```

<210> SEQ ID NO 3
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 3

Asp Asp Tyr Met Asn
1               5

<210> SEQ ID NO 4
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 4

```
gacgactata tgaat                                                        15
```

<210> SEQ ID NO 5
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 5

Trp Ile Asp Pro Glu Asn Gly Asp Thr Glu Tyr Ala Ser Lys Phe Gln
1               5                   10                  15
Gly

<210> SEQ ID NO 6
<211> LENGTH: 51
<212> TYPE: DNA
<213> ORGANISM: Artificial Sequence
<220> FEATURE:
<223> OTHER INFORMATION: Synthetic Polynucleotide

<400> SEQUENCE: 6

```
tggattgatc ctgagaatgg tgatactgaa tatgcctcga agttccaggg c                51
```

<210> SEQ ID NO 7
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 7

Gly Tyr Asp Tyr Phe Pro Phe Val Tyr
1               5

<210> SEQ ID NO 8
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 8
ggttatgatt acttcccctt tgtttac                                             27

<210> SEQ ID NO 9
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 9

Asp Val Leu Met Ser Gln Thr Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile His Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Lys Lys
            100                 105                 110

<210> SEQ ID NO 10
<211> LENGTH: 336
<212> TYPE: DNA
<213> ORGANISM: Artificial Sequence
<220> FEATURE:
<223> OTHER INFORMATION: Synthetic Polynucleotide

<400> SEQUENCE: 10
gatgttttga tgtcccaaac tccactctcc ctgcctgtca gtcttggaga tcaagcctcc     60
atctcttgca gatctagtca gaacattgta catagtaatg gaaacaccta tttagaatgg    120
tacctgcaga aaccaggcca gtctccaaag ctcctgatcc acaaagtttc caaccgattt    180
tctggggtcc cagacaggtt cagtggcagt ggatcaggga cagatttcac actcaagatc    240
agcagagtgg aggctgagga tctgggagtt tattactgct ttcaaggttc acatgttcca    300
ttcacgttcg gctcggggac taagttggaa aaaaaa                              336

<210> SEQ ID NO 11
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 11

Arg Ser Ser Gln Asn Ile Val His Ser Asn Gly Asn Thr Tyr Leu Glu
1               5                   10                  15

<210> SEQ ID NO 12
<211> LENGTH: 48
<212> TYPE: DNA
<213> ORGANISM: Artificial Sequence
<220> FEATURE:
<223> OTHER INFORMATION: Synthetic Polynucleotide

```
<400> SEQUENCE: 12
agatctagtc agaacattgt acatagtaat ggaaacacct atttagaa                48

<210> SEQ ID NO 13
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 13

Lys Val Ser Asn Arg Phe Ser
1               5

<210> SEQ ID NO 14
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 14
aaagtttcca accgattttc t                                             21

<210> SEQ ID NO 15
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 15

Phe Gln Gly Ser His Val Pro Phe Thr
1               5

<210> SEQ ID NO 16
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 16
tttcaaggtt cacatgttcc attcacg                                       27

<210> SEQ ID NO 17
<211> LENGTH: 119
<212> TYPE: PRT
<213> ORGANISM: Artificial Sequence
<220> FEATURE:
<223> OTHER INFORMATION: Synthetic Polypeptide

<400> SEQUENCE: 17

Gln Ile Gln Leu Val Gln Ser Gly Pro Glu Leu Lys Lys Pro Gly Glu
1               5                   10                  15

Thr Val Lys Ile Ser Cys Thr Thr Ser Gly Tyr Ile Phe Thr Thr Ser
            20                  25                  30

Gly Met Ser Trp Val Lys Gln Ala Pro Gly Lys Gly Leu Gln Trp Met
        35                  40                  45

Gly Trp Ile Asn Thr Tyr Ser Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80
```

Leu His Ile Asn Asp Leu Lys Asn Glu Asp Thr Ala Thr Tyr Phe Cys
                85                  90                  95

Ala Arg Ser Arg Asn Asn Tyr Glu Gly Phe Ala Tyr Trp Gly Gln Gly
            100                 105                 110

Thr Leu Val Thr Val Ser Val
        115

<210> SEQ ID NO 18
<211> LENGTH: 357
<212> TYPE: DNA
<213> ORGANISM: Artificial Sequence
<220> FEATURE:
<223> OTHER INFORMATION: Synthetic Polynucleotide

<400> SEQUENCE: 18
cagatccagt tggtacagtc tggacctgag ttgaagaagc ctggagagac agtcaagatc      60
tcctgcacga cttctgggta tattttcaca acctctggaa tgagctgggt gaaacaggct     120
ccaggaaagg gtttacagtg gatgggctgg ataaacacct attctggaga gccgacatat     180
gctgatgact tcaaggggcg gtttgccttc tctttggaaa cctctgccag cactgcctat     240
ttgcacatca cgacctcaa aaatgaggac acggccacat atttctgtgc aagatctagg      300
aataactacg aggggtttgc ttactggggc caagggactc tggtcactgt ctctgta        357

<210> SEQ ID NO 19
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 19

Thr Ser Gly Met Ser
1               5

<210> SEQ ID NO 20
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 20
acctctggaa tgagc                                                       15

<210> SEQ ID NO 21
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 21

Trp Ile Asn Thr Tyr Ser Gly Glu Pro Thr Tyr Ala Asp Asp Phe Lys
1               5                   10                  15

Gly

<210> SEQ ID NO 22
<211> LENGTH: 51
<212> TYPE: DNA
<213> ORGANISM: Artificial Sequence
<220> FEATURE:
<223> OTHER INFORMATION: Synthetic Polynucleotide

<400> SEQUENCE: 22
tggataaaca cctattctgg agagccgaca tatgctgatg acttcaaggg g    51

<210> SEQ ID NO 23
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 23

Ser Arg Asn Asn Tyr Glu Gly Phe Ala Tyr
1               5                   10

<210> SEQ ID NO 24
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 24
tctaggaata actacgaggg gtttgcttac    30

<210> SEQ ID NO 25
<211> LENGTH: 113
<212> TYPE: PRT
<213> ORGANISM: Artificial Sequence
<220> FEATURE:
<223> OTHER INFORMATION: Synthetic Polypeptide

<400> SEQUENCE: 25

Asp Ile Val Met Ser Gln Phe Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Phe Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Leu Tyr Pro Leu Thr Phe Gly Ala Gly Thr Lys Leu Glu Leu
            100                 105                 110

Lys

<210> SEQ ID NO 26
<211> LENGTH: 339
<212> TYPE: DNA
<213> ORGANISM: Artificial Sequence
<220> FEATURE:
<223> OTHER INFORMATION: Synthetic Polynucleotide

<400> SEQUENCE: 26
gacattgtga tgtcacagtt tccatcctcc ctagctgtgt cagttggaga gaaggttact    60
atgagctgca agtccagtca gagccttta tatagtagta atcaaaagaa ttatttggcc    120
tggttccagc agaaacccgg gcagtctcct aaactactga tttactgggc atccactagg    180
gaatctgggg tccctgatcg cttcacaggc agtggatctg ggacagattt cactctcacc    240

```
atcagcagtg tgaaggctga agacctggca gtttattact gtcagcaata ttatctctat    300
ccgctcacgt tcggtgctgg gaccaagctg gagctgaaa                            339
```

<210> SEQ ID NO 27
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 27

Lys Ser Ser Gln Ser Leu Leu Tyr Ser Ser Asn Gln Lys Asn Tyr Leu
1               5                   10                  15

Ala

<210> SEQ ID NO 28
<211> LENGTH: 51
<212> TYPE: DNA
<213> ORGANISM: Artificial Sequence
<220> FEATURE:
<223> OTHER INFORMATION: Synthetic Polynucleotide

<400> SEQUENCE: 28

```
aagtccagtc agagcctttt atatagtagt aatcaaaaga attatttggc c              51
```

<210> SEQ ID NO 29
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 29

Trp Ala Ser Thr Arg Glu Ser
1               5

<210> SEQ ID NO 30
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 30

```
tgggcatcca ctagggaatc t                                              21
```

<210> SEQ ID NO 31
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 31

Gln Gln Tyr Tyr Leu Tyr Pro Leu Thr
1               5

<210> SEQ ID NO 32
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 32
cagcaatatt atctctatcc gctcacg                                    27

<210> SEQ ID NO 33
<211> LENGTH: 687
<212> TYPE: PRT
<213> ORGANISM: Artificial Sequence
<220> FEATURE:
<223> OTHER INFORMATION: Synthetic Polypeptide

<400> SEQUENCE: 33

```
Met Val Ser Tyr Trp Asp Thr Gly Val Leu Leu Cys Ala Leu Leu Ser
 1               5                  10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Ile Asp Gln Ser Asn Ser His
        275                 280                 285

Ala Asn Ile Phe Tyr Ser Val Leu Thr Ile Asp Lys Met Gln Asn Lys
    290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
            340                 345                 350
```

Tyr Arg Leu Ser Met Lys Val Lys Ala Phe Pro Ser Pro Glu Val Val
            355                 360                 365

Trp Leu Lys Asp Gly Leu Pro Ala Thr Glu Lys Ser Ala Arg Tyr Leu
        370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
            420                 425                 430

Lys Ala Val Ser Ser Phe Pro Asp Pro Ala Leu Tyr Pro Leu Gly Ser
        435                 440                 445

Arg Gln Ile Leu Thr Cys Thr Ala Tyr Gly Ile Pro Gln Pro Thr Ile
    450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
                485                 490                 495

Asn Met Gly Asn Arg Ile Glu Ser Ile Thr Gln Arg Met Ala Ile Ile
            500                 505                 510

Glu Gly Lys Asn Lys Met Ala Ser Thr Leu Val Val Ala Asp Ser Arg
        515                 520                 525

Ile Ser Gly Ile Tyr Ile Cys Ile Ala Ser Asn Lys Val Gly Thr Val
    530                 535                 540

Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
                565                 570                 575

Cys Thr Val Asn Lys Phe Leu Tyr Arg Asp Val Thr Trp Ile Leu Leu
            580                 585                 590

Arg Thr Val Asn Asn Arg Thr Met His Tyr Ser Ile Ser Lys Gln Lys
        595                 600                 605

Met Ala Ile Thr Lys Glu His Ser Ile Thr Leu Asn Leu Thr Ile Met
    610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
                645                 650                 655

Gly Glu His Cys Asn Lys Lys Ala Val Phe Ser Arg Ile Ser Lys Phe
            660                 665                 670

Lys Ser Thr Arg Asn Asp Cys Thr Thr Gln Ser Asn Val Lys His
        675                 680                 685

<210> SEQ ID NO 34
<211> LENGTH: 2061
<212> TYPE: DNA
<213> ORGANISM: Artificial Sequence
<220> FEATURE:
<223> OTHER INFORMATION: Synthetic Polynucleotide

<400> SEQUENCE: 34
atggtcagct actgggacac cggggtcctg ctgtgcgcgc tgctcagctg tctgcttctc        60
acaggatcta gttccaggttc aaaattaaaa gatcctgaac tgagtttaaa aggcacccag       120
cacatcatgc aagcaggcca gacactgcat ctccaatgca gggggaagc agcccataaa        180

| tggtctttgc ctgaaatggt gagtaaggaa agcgaaaggc tgagcataac taaatctgcc | 240 |
| tgtggaagaa atggcaaaca attctgcagt actttaacct tgaacacagc tcaagcaaac | 300 |
| cacactggct tctacagctg caaatatcta gctgtaccta cttcaaagaa gaaggaaaca | 360 |
| gaatctgcaa tctatatatt tattagtgat acaggtagac ctttcgtaga gatgtacagt | 420 |
| gaaatccccg aaattataca catgactgaa ggaagggagc tcgtcattcc ctgccgggtt | 480 |
| acgtcaccta acatcactgt tactttaaaa aagtttccac ttgacacttt gatccctgat | 540 |
| gggaaacgca taatctggga cagtagaaag ggcttcatca tatcaaatgc aacgtacaaa | 600 |
| gaaatagggc ttctgacctg tgaagcaaca gtcaatgggc atttgtataa gacaaactat | 660 |
| ctcacacatc gacaaaccaa tacaatcata gatgtccaaa taagcacacc acgcccagtc | 720 |
| aaattactta gaggccatac tcttgtcctc aattgtactg ctaccactcc cttgaacacg | 780 |
| agagttcaaa tgacctggag ttaccctgat gaaaaaaata agagagcttc cgtaaggcga | 840 |
| cgaattgacc aaagcaattc ccatgccaac atattctaca gtgttcttac tattgacaaa | 900 |
| atgcagaaca aagacaaagg actttatact tgtcgtgtaa ggagtggacc atcattcaaa | 960 |
| tctgttaaca cctcagtgca tatatatgat aaagcattca tcactgtgaa acatcgaaaa | 1020 |
| cagcaggtgc ttgaaaccgt agctggcaag cggtcttacc ggctctctat gaaagtgaag | 1080 |
| gcatttccct cgccggaagt tgtatggtta aaagatgggt tacctgcgac tgagaaatct | 1140 |
| gctcgctatt tgactcgtgg ctactcgtta attatcaagg acgtaactga agaggatgca | 1200 |
| gggaattata caatcttgct gagcataaaa cagtcaaatg tgtttaaaaa cctcactgcc | 1260 |
| actctaattg tcaatgtgaa accccagatt tacgaaaagg ccgtgtcatc gtttccagac | 1320 |
| ccggctctct acccactggg cagcagacaa atcctgactt gtaccgcata tggtatccct | 1380 |
| caacctacaa tcaagtggtt ctggcacccc tgtaaccata atcattccga agcaaggtgt | 1440 |
| gacttttgtt ccaataatga agagtccttt atcctggatg ctgacagcaa catgggaaac | 1500 |
| agaattgaga gcatcactca gcgcatggca ataatagaag gaaagaataa gatggctagc | 1560 |
| accttggttg tggctgactc tagaatttct ggaatctaca tttgcatagc ttccaataaa | 1620 |
| gttgggactg tgggaagaaa cattagcttt tatatcacag atgtgccaaa tgggtttcat | 1680 |
| gttaacttgg aaaaaatgcc gacggaagga gaggacctga aactgtcttg cacagttaac | 1740 |
| aagttcttat acagagacgt tacttggatt ttactgcgga cagttaataa cagaacaatg | 1800 |
| cactacagta ttagcaagca aaaaatggcc atcactaagg agcactccat cactcttaat | 1860 |
| cttaccatca tgaatgtttc cctgcaagat tcaggcacct atgcctgcag agccaggaat | 1920 |
| gtatacacag gggaagaaat cctccagaag aaagaaatta caatcagagg tgagcactgc | 1980 |
| aacaaaaagg ctgttttctc tcggatctcc aaatttaaaa gcacaaggaa tgattgtacc | 2040 |
| acacaaagta atgtaaaaca t | 2061 |

<210> SEQ ID NO 35
<211> LENGTH: 2061
<212> TYPE: DNA
<213> ORGANISM: Artificial Sequence
<220> FEATURE:
<223> OTHER INFORMATION: Synthetic Polynucleotide

<400> SEQUENCE: 35

| atggtgagct actgggacac cggcgtgctg ctgtgcgccc tgctgagctg cctgctgctg | 60 |
| accggcagca gcagcggcag caagctgaag gaccctgagc tgagcctgaa gggcacccag | 120 |
| cacatcatgc aggccggcca gaccctgcac ctgcagtgcc gcggcgaggc cgcccacaag | 180 |

```
tggagcctgc cgagatggt gagcaaggag agcgagcgcc tgagcatcac caagagcgcc      240
tgcggccgca acggcaagca gttctgcagc accctgaccc tgaacaccgc ccaggccaac      300
cacaccggct tctacagctg caagtacctg gccgtgccca ccagcaagaa gaaggagacc      360
gagagcgcca tctacatctt catcagcgac accggccgcc ctttcgtgga gatgtacagc      420
gagatccctg agatcatcca catgaccgag ggccgcgagc tggtgatccc ttgccgcgtg      480
accagcccta catcaccgt gaccctgaag aagttccctc tggacaccct gatccctgac      540
ggcaagcgca tcatctggga cagccgcaag ggcttcatca tcagcaacgc cacctacaag      600
gagatcggcc tgctgacctg cgaggccacc gtgaacggcc acctgtacaa gaccaactac      660
ctgacccacc gccagaccaa caccatcatc gacgtgcaga tcagcacacc tcgccctgtg      720
aagctgctgc gcggccacac cctggtgctg aactgcaccg ccaccactcc tctgaacacc      780
cgcgtgcaga tgacctggag ctaccctgac gagaagaaca agcgcgccag cgtgcgccgc      840
cgcatcgacc agagcaacag ccacgccaac atcttctaca gcgtgctgac catcgacaag      900
atgcagaaca aggacaaggg cctgtacacc tgccgcgtgc gcagcggccc tagcttcaag      960
agcgtgaaca ccagcgtgca catctacgac aaggccttca tcaccgtgaa gcaccgcaag     1020
cagcaggtgc tggagaccgt ggccggcaag cgcagctacc gcctgagcat gaaggtgaag     1080
gccttcccta gccctgaggt ggtgtggctg aaggacggcc tgcccgccac cgagaagagc     1140
gcccgctacc tgacccgcgg ctacagcctg atcatcaagg acgtgaccga ggaggacgcc     1200
ggcaactaca ccatcctgct gagcatcaag cagagcaacg tgttcaagaa cctgaccgcc     1260
accctgatcg tgaacgtgaa gcctcagatc tacgagaagg ccgtgagcag cttccctgac     1320
cctgccctgt accctctggg cagccgccag atcctgacct gcaccgccta cggcatccct     1380
cagcccacca tcaagtggtt ctggcaccct tgcaaccaca accacagcga ggcccgctgc     1440
gacttctgca gcaacaacga ggagagcttc atcctggacg ccgacagcaa catgggcaac     1500
cgcatcgaga gcatcaccca gcgcatggcc atcatcgagg gcaagaacaa gatggccagc     1560
accctggtgg tggccgacag ccgcatcagc ggcatctaca tctgcatcgc cagcaacaag     1620
gtgggcaccg tgggccgcaa catcagcttc tacatcaccg acgtgcccaa cggcttccac     1680
gtgaacctgg agaagatgcc caccgagggc gaggacctga agctgagctg caccgtgaac     1740
aagttcctgt accgcgacgt gacctggatc ctgctgcgca ccgtgaacaa ccgcaccatg     1800
cactacagca tcagcaagca gaagatggcc atcaccaagg agcacagcat cccctgaac     1860 ctgaccatca tgaacgtgag cctgcaggac agcggcacct acgcctgccg cgcccgcaac     1920
gtgtacaccg gcgaggagat cctgcagaag aaggagatca ccatccgcgg cgagcactgc     1980
aacaagaagg ccgtgttcag ccgcatcagc aagttcaaga gcacccgcaa cgactgcacc     2040
acccagagca acgtgaagca c                                                2061
```

<210> SEQ ID NO 36
<211> LENGTH: 733
<212> TYPE: PRT
<213> ORGANISM: Artificial Sequence
<220> FEATURE:
<223> OTHER INFORMATION: Synthetic Polypeptide

<400> SEQUENCE: 36

```
Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
```

```
            20                  25                  30
Glu Leu Ser Leu Lys Gly Thr Gln His Ile Met Gln Ala Gly Gln Thr
            35                  40                  45
Leu His Leu Gln Cys Arg Gly Glu Ala Ala His Lys Trp Ser Leu Pro
        50                  55                  60
Glu Met Val Ser Lys Glu Ser Glu Arg Leu Ser Ile Thr Lys Ser Ala
65                  70                  75                  80
Cys Gly Arg Asn Gly Lys Gln Phe Cys Ser Thr Leu Thr Leu Asn Thr
                85                  90                  95
Ala Gln Ala Asn His Thr Gly Phe Tyr Ser Cys Lys Tyr Leu Ala Val
                100                 105                 110
Pro Thr Ser Lys Lys Lys Glu Thr Glu Ser Ala Ile Tyr Ile Phe Ile
            115                 120                 125
Ser Asp Thr Gly Arg Pro Phe Val Glu Met Tyr Ser Glu Ile Pro Glu
        130                 135                 140
Ile Ile His Met Thr Glu Gly Arg Glu Leu Val Ile Pro Cys Arg Val
145                 150                 155                 160
Thr Ser Pro Asn Ile Thr Val Thr Leu Lys Lys Phe Pro Leu Asp Thr
                165                 170                 175
Leu Ile Pro Asp Gly Lys Arg Ile Ile Trp Asp Ser Arg Lys Gly Phe
                180                 185                 190
Ile Ile Ser Asn Ala Thr Tyr Lys Glu Ile Gly Leu Leu Thr Cys Glu
                195                 200                 205
Ala Thr Val Asn Gly His Leu Tyr Lys Thr Asn Tyr Leu Thr His Arg
        210                 215                 220
Gln Thr Asn Thr Ile Ile Asp Val Gln Ile Ser Thr Pro Arg Pro Val
225                 230                 235                 240
Lys Leu Leu Arg Gly His Thr Leu Val Leu Asn Cys Thr Ala Thr Thr
                245                 250                 255
Pro Leu Asn Thr Arg Val Gln Met Thr Trp Ser Tyr Pro Asp Glu Lys
                260                 265                 270
Asn Lys Arg Ala Ser Val Arg Arg Ile Asp Gln Ser Asn Ser His
        275                 280                 285
Ala Asn Ile Phe Tyr Ser Val Leu Thr Ile Asp Lys Met Gln Asn Lys
        290                 295                 300
Asp Lys Gly Leu Tyr Thr Cys Arg Val Arg Ser Gly Pro Ser Phe Lys
305                 310                 315                 320
Ser Val Asn Thr Ser Val His Ile Tyr Asp Lys Ala Phe Ile Thr Val
                325                 330                 335
Lys His Arg Lys Gln Gln Val Leu Glu Thr Val Ala Gly Lys Arg Ser
                340                 345                 350
Tyr Arg Leu Ser Met Lys Val Lys Ala Phe Pro Ser Pro Glu Val Val
            355                 360                 365
Trp Leu Lys Asp Gly Leu Pro Ala Thr Glu Lys Ser Ala Arg Tyr Leu
        370                 375                 380
Thr Arg Gly Tyr Ser Leu Ile Ile Lys Asp Val Thr Glu Glu Asp Ala
385                 390                 395                 400
Gly Asn Tyr Thr Ile Leu Leu Ser Ile Lys Gln Ser Asn Val Phe Lys
                405                 410                 415
Asn Leu Thr Ala Thr Leu Ile Val Asn Val Lys Pro Gln Ile Tyr Glu
                420                 425                 430
Lys Ala Val Ser Ser Phe Pro Asp Pro Ala Leu Tyr Pro Leu Gly Ser
            435                 440                 445
```

```
Arg Gln Ile Leu Thr Cys Thr Ala Tyr Gly Ile Pro Gln Pro Thr Ile
        450                 455                 460
Lys Trp Phe Trp His Pro Cys Asn His Asn His Ser Glu Ala Arg Cys
465                 470                 475                 480
Asp Phe Cys Ser Asn Asn Glu Glu Ser Phe Ile Leu Asp Ala Asp Ser
                485                 490                 495
Asn Met Gly Asn Arg Ile Glu Ser Ile Thr Gln Arg Met Ala Ile Ile
            500                 505                 510
Glu Gly Lys Asn Lys Met Ala Ser Thr Leu Val Val Ala Asp Ser Arg
        515                 520                 525
Ile Ser Gly Ile Tyr Ile Cys Ile Ala Ser Asn Lys Val Gly Thr Val
        530                 535                 540
Gly Arg Asn Ile Ser Phe Tyr Ile Thr Asp Val Pro Asn Gly Phe His
545                 550                 555                 560
Val Asn Leu Glu Lys Met Pro Thr Glu Gly Glu Asp Leu Lys Leu Ser
                565                 570                 575
Cys Thr Val Asn Lys Phe Leu Tyr Arg Asp Val Thr Trp Ile Leu Leu
            580                 585                 590
Arg Thr Val Asn Asn Arg Thr Met His Tyr Ser Ile Ser Lys Gln Lys
        595                 600                 605
Met Ala Ile Thr Lys Glu His Ser Ile Thr Leu Asn Leu Thr Ile Met
610                 615                 620
Asn Val Ser Leu Gln Asp Ser Gly Thr Tyr Ala Cys Arg Ala Arg Asn
625                 630                 635                 640
Val Tyr Thr Gly Glu Glu Ile Leu Gln Lys Lys Glu Ile Thr Ile Arg
                645                 650                 655
Asp Gln Glu Ala Pro Tyr Leu Leu Arg Asn Leu Ser Asp His Thr Val
            660                 665                 670
Ala Ile Ser Ser Ser Thr Thr Leu Asp Cys His Ala Asn Gly Val Pro
        675                 680                 685
Glu Pro Gln Ile Thr Trp Phe Lys Asn Asn His Lys Ile Gln Gln Glu
        690                 695                 700
Pro Glu Leu Tyr Thr Ser Thr Ser Pro Ser Ser Ser Ser Ser Ser Pro
705                 710                 715                 720
Leu Ser Ser Ser Ser Ser Ser Ser Ser Ser Ser Ser
                725                 730

<210> SEQ ID NO 37
<211> LENGTH: 2199
<212> TYPE: DNA
<213> ORGANISM: Artificial Sequence
<220> FEATURE:
<223> OTHER INFORMATION: Synthetic Polynucleotide

<400> SEQUENCE: 37
atggtcagct actgggacac cggggtcctg ctgtgcgcgc tgctcagctg tctgcttctc      60
acaggatcta gttcaggttc aaaattaaaa gatcctgaac tgagtttaaa aggcacccag     120
cacatcatgc aagcaggcca gacactgcat ctccaatgca gggggaagc agcccataaa     180 tggtctttgc ctgaaatggt gagtaaggaa agcgaaaggc tgagcataac taatctgcc     240 tgtggaagaa atgcaaaaca attctgcagt actttaacct tgaacacagc tcaagcaaac     300
cacactggct tctacagctg caaatatcta gctgtaccta cttcaaagaa gaaggaaaca     360
gaatctgcaa tctatatatt tattagtgat acaggtagac ctttcgtaga gatgtacagt     420
```

```
gaaatccccg aaattataca catgactgaa ggaagggagc tcgtcattcc ctgccgggtt      480
acgtcaccta acatcactgt tactttaaaa aagtttccac ttgacacttt gatccctgat      540
ggaaaacgca taatctggga cagtagaaag ggcttcatca tatcaaatgc aacgtacaaa      600
gaaatagggc ttctgacctg tgaagcaaca gtcaatgggc atttgtataa gacaaactat      660
ctcacacatc gacaaaccaa tacaatcata gatgtccaaa taagcacacc acgcccagtc      720
aaattactta gaggccatac tcttgtcctc aattgtactg ctaccactcc cttgaacacg      780
agagttcaaa tgacctggag ttaccctgat gaaaaaaata gagagcttc cgtaaggcga      840
cgaattgacc aaagcaattc ccatgccaac atattctaca gtgttcttac tattgacaaa      900
atgcagaaca aagacaaagg actttatact tgtcgtgtaa ggagtggacc atcattcaaa      960
tctgttaaca cctcagtgca tatatatgat aaagcattca tcactgtgaa acatcgaaaa     1020
cagcaggtgc ttgaaaccgt agctggcaag cggtcttacc ggctctctat gaaagtgaag     1080
gcatttcct cgccggaagt tgtatggtta aaagatgggt tacctgcgac tgagaaatct      1140
gctcgctatt tgactcgtgg ctactcgtta attatcaagg acgtaactga agaggatgca     1200
gggaattata caatcttgct gagcataaaa cagtcaaatg tgtttaaaaa cctcactgcc     1260
actctaattg tcaatgtgaa accccagatt tacgaaaagg ccgtgtcatc gtttccagac     1320
ccggctctct acccactggg cagcagacaa atcctgactt gtaccgcata tggtatccct     1380
caacctacaa tcaagtggtt ctggcacccc tgtaaccata atcattccga agcaaggtgt     1440
gacttttgtt ccaataatga agagtccttt atcctggatg ctgacagcaa catgggaaac     1500
agaattgaga gcatcactca gcgcatggca ataatagaag gaaagaataa gatggctagc     1560
accttggttg tggctgactc tagaatttct ggaatctaca tttgcatagc ttccaataaa     1620
gttgggactg tgggaagaaa cataagcttt tatatcacag atgtgccaaa tgggtttcat     1680
gttaacttgg aaaaaatgcc gacagaagga gaggacctga actgtcttg cacagttaac     1740
aagttcttat acagagacgt tacttggatt ttactgcgga cagttaataa cagaacaatg     1800
cactacagta ttagcaagca aaaaatggcc atcactaagg agcactccat cactcttaat     1860
cttaccatca tgaatgtttc cctgcaagat tcaggcacct atgcctgcag agccaggaat     1920
gtatacacag gggaagaaat cctccagaag aaagaaatta caatcagaga tcaggaagca     1980
ccatacctcc tgcgaaacct cagtgatcac acagtggcca tcagcagttc caccactta      2040
gactgtcatg ctaatggtgt ccccgagcct cagatcactt ggtttaaaaa caaccacaaa     2100
atacaacaag agcctgaact gtatacatca acgtcaccat cgtcatcgtc atcatcacca     2160
ttgtcatcat catcatcatc gtcatcatca tcatcatca                            2199
```

<210> SEQ ID NO 38
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 38

Glu His Cys Asn Lys Lys Ala Val Phe Ser Arg Ile Ser Lys Phe Lys
1               5                   10                  15

Ser Thr Arg Asn Asp Cys Thr Thr Gln Ser Asn Val Lys His
            20                  25                  30

<210> SEQ ID NO 39
<211> LENGTH: 90

-continued

```
<212> TYPE: DNA
<213> ORGANISM: Artificial Sequence
<220> FEATURE:
<223> OTHER INFORMATION: Synthetic Polynucleotide

<400> SEQUENCE: 39
gaacactgca ataaaaaggc tgttttttcc cgtatttcga aatttaaaag cacacgcaat    60
gactgtacga ctcaaagtaa tgtgaagcat                                    90

<210> SEQ ID NO 40
<211> LENGTH: 49
<212> TYPE: PRT
<213> ORGANISM: Artificial Sequence
<220> FEATURE:
<223> OTHER INFORMATION: Synthetic Polypeptide

<400> SEQUENCE: 40

Asp Gln Glu Ala Pro Tyr Leu Leu Arg Asn Leu Ser Asp His Thr Val
1               5                   10                  15

Ala Ile Ser Ser Ser Thr Thr Leu Asp Cys His Ala Asn Gly Val Pro
            20                  25                  30

Glu Pro Gln Ile Thr Trp Phe Lys Asn Asn His Lys Ile Gln Gln Glu
        35                  40                  45

Pro

<210> SEQ ID NO 41
<211> LENGTH: 147
<212> TYPE: DNA
<213> ORGANISM: Artificial Sequence
<220> FEATURE:
<223> OTHER INFORMATION: Synthetic Polynucleotide

<400> SEQUENCE: 41
gatcaggaag caccatacct cctgcgaaac ctcagtgatc acacagtggc catcagcagt    60
tccaccactt tagactgtca tgctaatggt gtccccgagc ctcagatcac ttggtttaaa   120
aacaaccaca aaatacaaca agagcct                                      147

<210> SEQ ID NO 42
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 42

Cys Asp Gln Glu Ala Pro Tyr Leu Leu Arg Asn Leu Ser Asp His
1               5                   10                  15

<210> SEQ ID NO 43
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 43

Cys Asn Lys Lys Ala Val Phe Ser Arg Ile Ser Lys Phe Lys Ser Thr
1               5                   10                  15

Arg Asn

<210> SEQ ID NO 44
<211> LENGTH: 56
```

```
<212> TYPE: PRT
<213> ORGANISM: Artificial Sequence
<220> FEATURE:
<223> OTHER INFORMATION: Synthetic Polypeptide

<400> SEQUENCE: 44

Lys Glu Ile Thr Ile Arg Asp Gln Glu Ala Pro Tyr Leu Leu Arg Asn
1               5                   10                  15

Leu Ser Asp His Thr Val Ala Ile Ser Ser Thr Thr Leu Asp Cys
            20                  25                  30

His Ala Asn Gly Val Pro Glu Pro Gln Ile Thr Trp Phe Lys Asn Asn
        35                  40                  45

His Lys Ile Gln Gln Glu Pro Gly
        50                  55

<210> SEQ ID NO 45
<211> LENGTH: 37
<212> TYPE: PRT
<213> ORGANISM: Artificial Sequence
<220> FEATURE:
<223> OTHER INFORMATION: Synthetic Polypeptide

<400> SEQUENCE: 45

Lys Glu Ile Thr Ile Arg Gly Glu His Cys Asn Lys Lys Ala Val Phe
1               5                   10                  15

Ser Arg Ile Ser Lys Phe Lys Ser Thr Arg Asn Asp Cys Thr Thr Gln
            20                  25                  30

Ser Asn Val Lys His
        35
```